(12) United States Patent
Kawasaki et al.

(10) Patent No.: US 11,980,417 B2
(45) Date of Patent: May 14, 2024

(54) IMAGE DISPLAY DEVICE, IMAGE DISPLAY SYSTEM, IMAGE DISPLAY METHOD, IMAGE PROCESSING PROGRAM STORAGE MEDIUM

(71) Applicant: NIKON CORPORATION, Tokyo (JP)

(72) Inventors: Tomohiro Kawasaki, Yokohama (JP); Ryoichi Sataka, Yokohama (JP); Masahiro Mizuta, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 743 days.

(21) Appl. No.: 17/097,322

(22) Filed: Nov. 13, 2020

(65) Prior Publication Data

US 2021/0059515 A1 Mar. 4, 2021

Related U.S. Application Data

(63) Continuation of application No. PCT/JP2019/016706, filed on Apr. 18, 2019.

(30) Foreign Application Priority Data

May 14, 2018 (JP) .................................. 2018-093048

(51) Int. Cl.
*A61B 3/00* (2006.01)
*A61B 3/12* (2006.01)
*G06T 3/60* (2006.01)

(52) U.S. Cl.
CPC .......... *A61B 3/0058* (2013.01); *A61B 3/0075* (2013.01); *A61B 3/12* (2013.01); *G06T 3/60* (2013.01)

(58) Field of Classification Search
CPC ....... A61B 3/0058; A61B 3/0075; A61B 3/12; A61B 3/112; A61B 3/14; A61B 3/08; G06T 3/60; G02B 27/02
(Continued)

(56) References Cited

U.S. PATENT DOCUMENTS 5,384,654 A * 1/1995 Iba ........................ G02B 27/017
359/740
5,757,544 A * 5/1998 Tabata ................ G02B 27/0172
359/666
(Continued)

FOREIGN PATENT DOCUMENTS

JP 2000-214388 A 8/2000
JP 2006-346106 A 12/2006
(Continued)

OTHER PUBLICATIONS

International Search Report, PCT/ISA/210, dated Jun. 18, 2019, in corresponding International Patent Application No. PCT/JP2019/016706.
(Continued)

*Primary Examiner* — Mohammed A Hasan

(57) ABSTRACT

In an ophthalmology system, an right-eye imaged image is displayed on a display section for presentation to an observer through an optical unit and a reflection member. A left-eye imaged image is also displayed on a display section for presentation to an observer through an optical unit and a reflection member. A separation between the left and right imaged images is made wider than a spacing between the left and right optical units. This enables image presentation with the optical axes for the observer viewing the images intersecting in front so as to cause a convergence angle to arise.

20 Claims, 31 Drawing Sheets

(58) Field of Classification Search
USPC .......................................................... 351/206
See application file for complete search history.

(56) References Cited

U.S. PATENT DOCUMENTS

| | | | |
|---|---|---|---|
| 7,206,135 B2* | 4/2007 | Yamazaki | G02B 17/0848 |
| | | | 359/630 |
| 2002/0051118 A1* | 5/2002 | Takagi | G02B 27/0172 |
| | | | 348/E13.047 |
| 2011/0025824 A1* | 2/2011 | Kato | G03B 35/00 |
| | | | 396/326 |
| 2011/0164294 A1* | 7/2011 | Shimizu | G02B 27/0172 |
| | | | 359/13 |

FOREIGN PATENT DOCUMENTS

| | | | |
|---|---|---|---|
| JP | 2009-288696 A | 12/2009 | |
| JP | 2010-231192 A | 10/2010 | |
| JP | 2013-254125 A | 12/2013 | |

OTHER PUBLICATIONS

Written Opinion of the International Searching Authority, PCT/ISA/237, dated Jun. 18, 2019, in corresponding International Patent Application No. PCT/JP2019/016706.

* cited by examiner

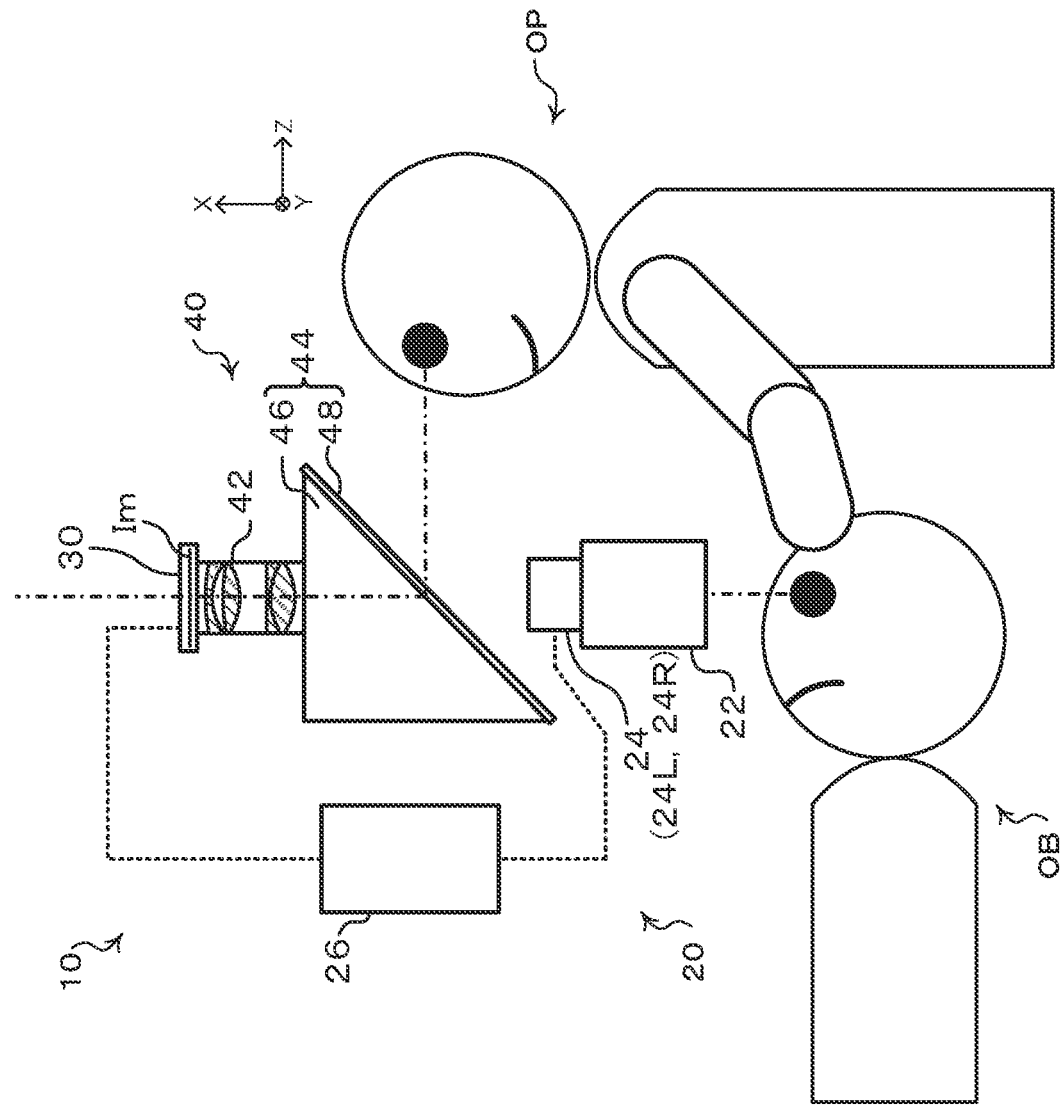

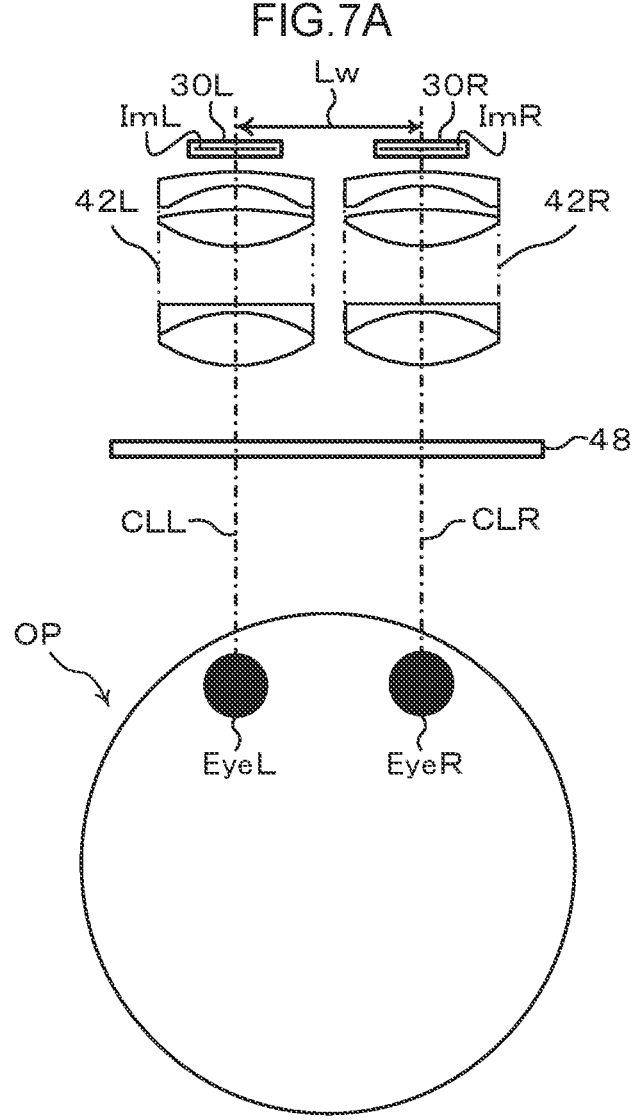

FIG.13
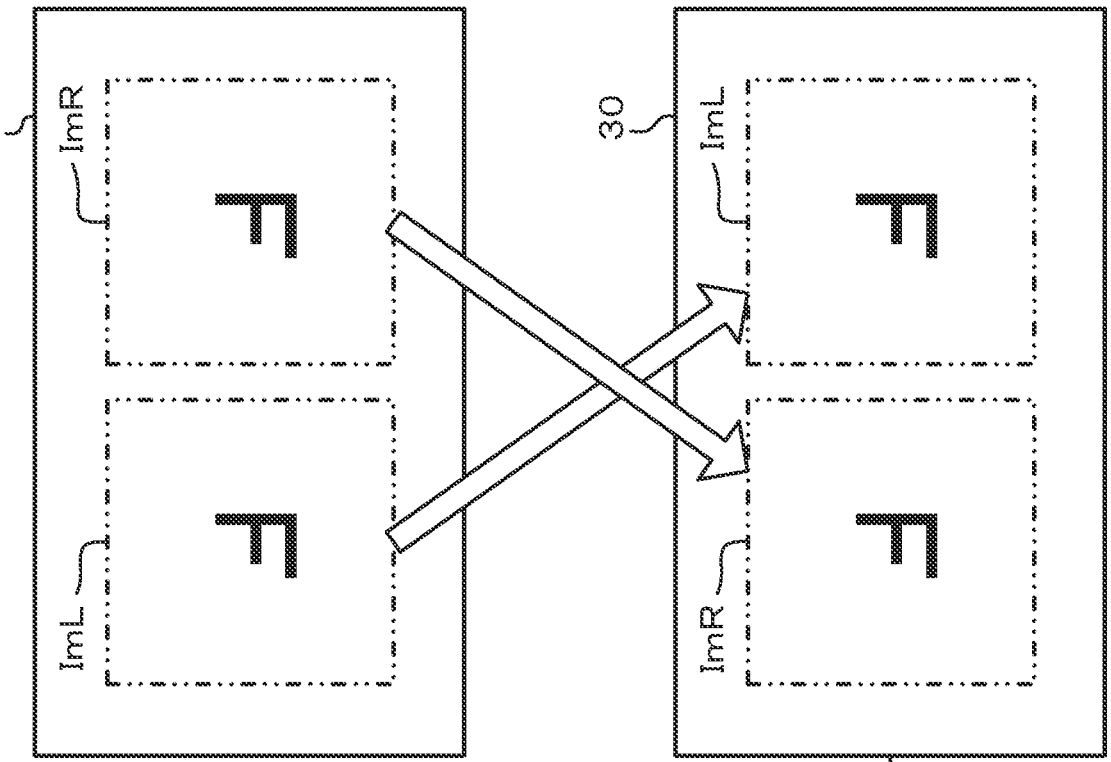
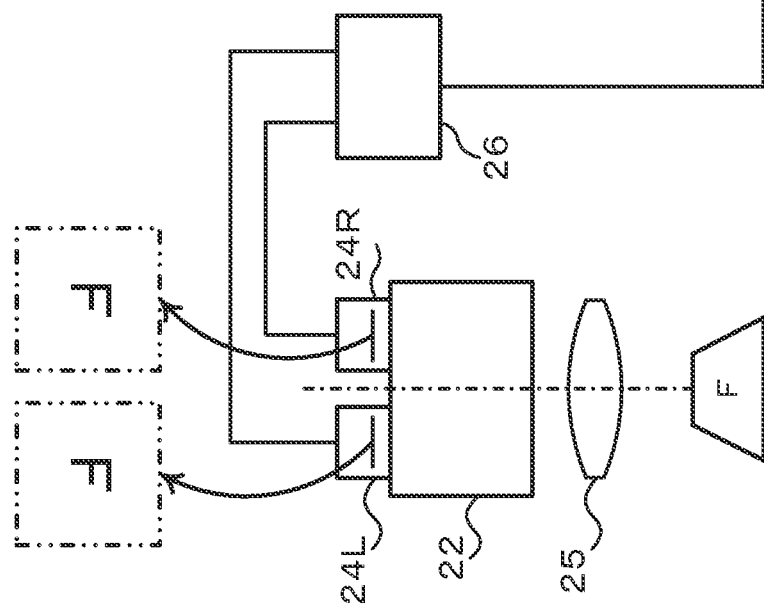

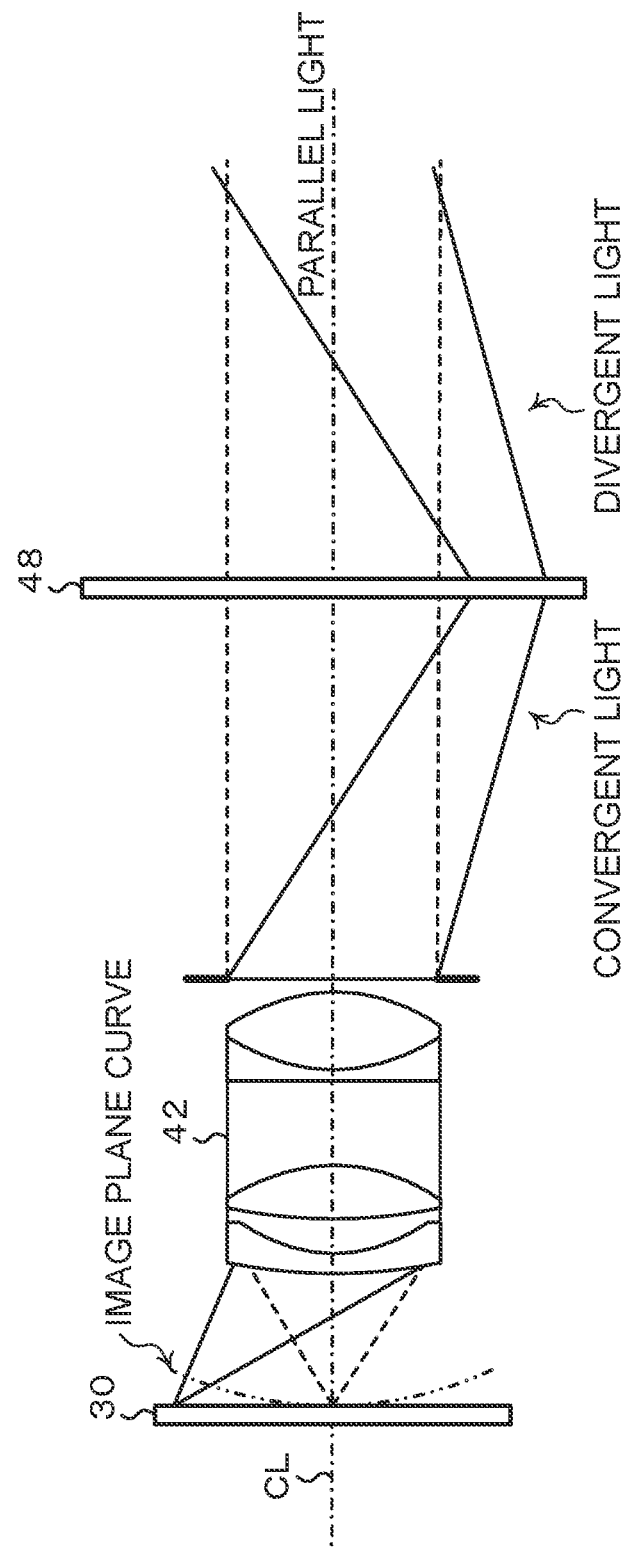

IMAGE DISPLAY DEVICE, IMAGE DISPLAY SYSTEM, IMAGE DISPLAY METHOD, IMAGE PROCESSING PROGRAM STORAGE MEDIUM

CROSS-REFERENCE TO RELATED APPLICATION

This application is a continuation application of International Application No. PCT/JP2019/016706, filed Apr. 18, 2019, the disclosure of which is incorporated herein by reference in its entirety. Further, this application claims priority from Japanese Patent Application No. 2018-093048, filed May 14, 2018, the disclosure of which is incorporated herein by reference in its entirety.

BACKGROUND

Technical Field

Technology disclosed herein relates to an image display device, an image display system, an image display method, and an image processing program storage medium.

Related Art

In ophthalmology there are various implementations of ophthalmic devices capable of observing the eyes of subjects (hereafter referred to as examined eyes) for the purpose of ophthalmic diagnostics and surgical treatment of the eyes. Moreover, recently ophthalmic devices capable of observing an examined eye with binocular vision are also been implemented. In the present specification "ophthalmology" refers to the medical field for treating eyes. Technology related to image display devices capable of observing objects such as an examined eye with binocular vision is also known (see Japanese Patent Application Laid-Open (JP-A) No. 2009-288696).

In the technology described in JP-A No. 2009-288696, a virtual image is formed for a real image projected by projector using a reflection element that includes functionality to perform spatial replication twice on incident light, as an optical system that does not require a screen.

SUMMARY

A first aspect of technology disclosed herein is an image display device including a left-eye optical unit, a right-eye optical unit, a display section, and a reflection section. In the left-eye optical unit a left-eye image region for displaying a left-eye image is disposed on an incident side of the left-eye optical unit and a left-eye exit pupil is formed outside an outermost lens on an exit side of the left-eye optical unit. In the right-eye optical unit a right-eye image region for displaying a right-eye image is disposed on an incident side of the right-eye optical unit and a right-eye exit pupil is formed outside an outermost lens on an exit side of the right-eye optical unit. The display section causes a convergence angle to arise between two eyes when the left-eye image region is viewed through the left-eye optical unit and the right-eye image region is viewed through the right-eye optical unit by presenting the left-eye image region such that its region center is disposed in a focal plane of the left-eye optical unit at a position away from an optical axis of the left-eye optical unit, and by presenting the right-eye image region such that its region center is disposed in a focal plane of the right-eye optical unit at a position away from an optical axis of the right-eye optical unit. The reflection section reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

A second aspect of technology disclosed herein is an image display device including a left-eye optical unit, a right-eye optical unit, a display section, and a reflection section. In the left-eye optical unit a left-eye image region for displaying a left-eye image is disposed on an incident side of the left-eye optical unit and a left-eye exit pupil is formed outside an outermost lens on an exit side of the left-eye optical unit. In the right-eye optical unit a right-eye image region for displaying a right-eye image is disposed on an incident side of the right-eye optical unit and a right-eye exit pupil is formed outside an outermost lens on an exit side of the right-eye optical unit. The display section causes a convergence angle to arise between two eyes when the left-eye image region is viewed through the left-eye optical unit and the right-eye image region is viewed through the right-eye optical unit by presenting the left-eye image region such that its region center is disposed in a focal plane of the left-eye optical unit and on an optical axis of the left-eye optical unit, and by presenting the right-eye image region such that its region center is disposed in a focal plane of the right-eye optical unit and on an optical axis of the right-eye optical unit. The display section causes the optical axis of the left-eye optical unit and the optical axis of the right-eye optical unit to intersect each other at the exit sides of the left-eye optical unit and the right-eye optical unit. The reflection section reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

A third aspect of technology disclosed herein is an image display device including an optical unit, an optical element, and a convergence angle adjustment mechanism. The optical unit includes a focal point on a light incident side at a position where an image of an object is displayed on a display section and forms an exit pupil. The optical element is configured to reflect light emitted from the optical unit or to allow light emitted from the optical unit to pass through and to relay the exit pupil to a position having a conjugate relationship to the exit pupil. The convergence angle adjustment mechanism is configured to cause a convergence angle to arise between the two eyes of an observer observing at the position of the exit pupil relayed by the optical element.

A fourth aspect of technology disclosed herein is an image display system including the image display device, and an image processing section configured to acquire right-eye image information and left-eye image information and to perform image processing such that a right-eye image region and a left-eye image region formed based on the acquired right-eye image information and the acquired left-eye image information are inverted.

A fifth aspect of technology disclosed herein is an image display method of the image display device. The image display method executes processing including presenting an inverted state of a right-eye image region and a left-eye image region formed based on right-eye image information and left-eye image information.

A sixth aspect of technology disclosed herein is a non-transitory storage medium stored with an image processing program to cause a computer to function as an image processing section of the image display device.

A seventh aspect of technology disclosed herein is a non-transitory storage medium stored with an image processing program to cause a computer to function as the image processing section of the image display system.

BRIEF DESCRIPTION OF THE DRAWINGS

FIG. 1 is a block diagram illustrating an example of an overall configuration of an ophthalmic system according to an exemplary embodiment.

FIG. 7A is a schematic diagram illustrating an example of optical paths in a display device according to an exemplary embodiment, and illustrates a display device in which optical axes of a left-eye optical unit and a right-eye optical unit are parallel to each other.

FIG. 13 is an illustration illustrating an example of imaged images displayed in a case in which a front-end lens that forms a primary image is employed to observe a posterior eye portion of an examined eye using an ophthalmic system according to an exemplary embodiment.

FIG. 18 is a schematic diagram illustrating an example of a positional relationship between a display device and an optical unit according to an exemplary embodiment.

DETAILED DESCRIPTION

Figure 2A:
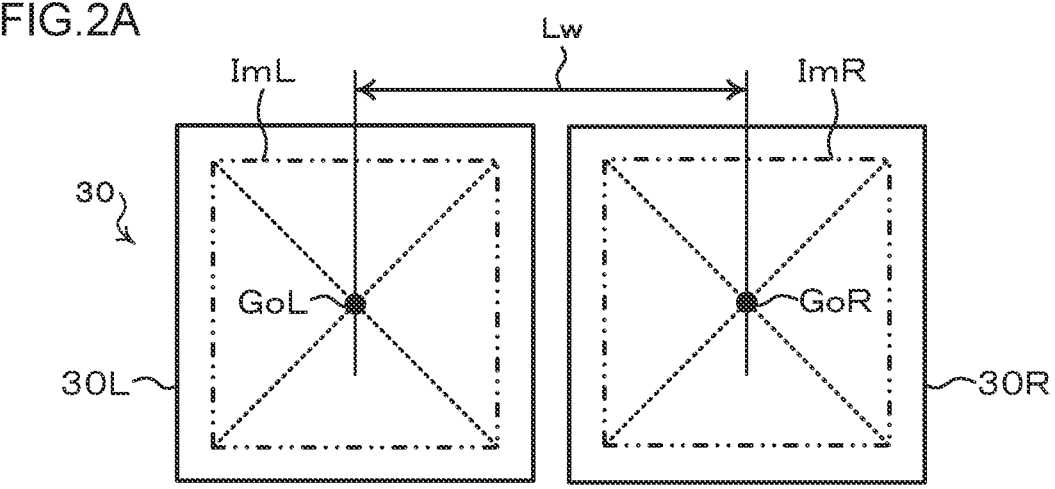
FIG. 2A is an illustration illustrating an example of a relationship between an imaging device and a display device for binocular vision according to an exemplary embodiment, illustrating a case in which a left-eye image and a right-eye image are displayed independently.

Explanation follows regarding exemplary embodiments, with reference to the drawings.

In the technology disclosed herein, an image display device according to technology disclosed herein is applicable to any device for displaying images, and an image display system according to technology disclosed herein is applicable to any system equipped with a device for displaying images. In the present exemplary embodiment, for ease of explanation, as an example of an image display system provided with an image display device for image display, a case will be described of an ophthalmic system applied with an ophthalmic device, for an observer such as a doctor to observe an eye (hereafter examined eye) of a patient or the like and the periphery of the examined eye for the purpose of ophthalmic diagnostics and surgical treatment of the eyes in ophthalmology.

Although in the following explanation an example of an image display system will be described, the technology disclosed herein is not limited to an ophthalmic system applied with an ophthalmic device. Namely, there is no limitation to an image display device to display an image imaged by an imaging device employed in ophthalmology to image an examined eye and a periphery of the examined eye, and application may be made to any image display device and image display system in which an object is imaged and the imaged image displayed, without limitation to ophthalmology. For example, in medical fields, application may be made to image display devices and image display systems employed in any field of medicine. Moreover, the technology disclosed herein is not limited to an image display device or image display system employed in any medical field, and is obviously applicable to any image display device and image display system capable of displaying images.

Moreover, although a description follows in the present exemplary embodiment of a case in which an image imaged by an imaging device of an examined eye and the periphery of the examined eye is employed as an imaged image and the imaged image is displayed, as an example of a case in which the technology disclosed herein is applied, the imaged image may be a still image, and may also be a video image. Moreover, the image employed in the present exemplary embodiment is not limited to an imaged image. Namely, employing an image imaged by an imaging device as the imaged image is merely an example of technology disclosed herein. For example, the technology disclosed herein is also applicable to an image display device and an image display system for displaying pre-prepared images.

Furthermore, as an example of application of an ophthalmic system, an example will be described of an ophthalmic surgical microscope employed when an observer such as a doctor operates while observing the examined eye and the periphery of the examined eye. The application in this case to an ophthalmic surgical microscope is also merely an example of an image display system according to technology disclosed herein, and in medical fields, application may be made to surgical microscopes employed in any field of medicine. The image display system according to the technology disclosed herein is also not limited to a surgical microscope employed in a medical field, and obviously application may be made to another optical device including a microscope for observing objects.

FIG. 1 illustrates an example of a configuration of an ophthalmic system 10 according to the present exemplary embodiment.

As illustrated in FIG. 1, the ophthalmic system 10 includes an imaging section 20 to image the examined eye and periphery of the examined eye as an object OB containing biological tissue, a display section 30, such as a display, to display the image imaged with the imaging section 20, and a display device 40 used to display to an observer OP the imaged image of the display section 30. In the ophthalmic system 10, the examined eye and the periphery of the examined eye of the observation subject is imaged by the imaging section 20, the image imaged thereby is formed on the display section 30, and the imaged image is displayed for the observer OP using the display device 40. A display section 30 such as a display is detachably attached to the display device 40, such that the display device 40 is formed including the display section 30.

The imaging section 20 is equipped with a microscope 22, a camera 24, and a camera controller 26. The microscope 22 is an optical system to observer the object OB, i.e. the examined eye and the periphery of the examined eye. The camera 24 is an electronic device for converting images produced by the microscope 22 of the object OB, i.e. the examined eye and the periphery of the examined eye, into a picture signal. The camera controller 26 is an electronic device for converting the picture signal into a display signal and outputting the display signal. The camera controller 26 is connected to the display section 30, a typical example thereof being a liquid crystal monitor or the like, and outputs a display signal to the display section 30. The image imaged by the camera 24 is thereby formed as an imaged image Im on the display section 30. The observer OP operates the microscope 22 while viewing an image displayed on the display device 40, and sets the microscope 22 at an observation position to observe the object OB i.e. the examined eye and the periphery of the examined eye.

The display device 40 is equipped with an optical unit 42 and a reflection section 44. The optical unit 42 is an example of an optical unit of technology disclosed herein, and functions as an objective lens to refract at least light from the incident imaged image Im and to emit the refracted light (described in detail later). The reflection section 44 includes a case 46 and a reflection member 48. The display device 40 is attached to a stand, omitted from illustration, is formed so as to be independent from the imaging section 20, and is formed so as to be in a non-contact state with the observer OP. Forming the display device 40 so as to be in a non-contact state with the observer OP suppresses the observer OP from feeling unsettled by contact occurring of the observer OP with the display device 40.

In the ophthalmic system 10, the imaging section 20, and the display section 30-equipped display device 40, are independently formed from each other, enabling separate respective movements thereof. Thus even in cases in which the imaging section 20 has been moved to change the observation position while the observer OP is viewing the object OB (for example the examined eye and the periphery of the examined eye) using the display device 40, the display device does not move, and so the observer OP is able to view the imaged image Im without head movement. This is advantageous in terms of operation in cases such as those in which an ophthalmic surgical microscope is applied as the imaging section 20. For example, in cases in which operating is being performed while moving the operating field, the observer OP such as a doctor is able to concentrate on operating while inspecting the operating field without changing viewing position. Moreover, due to being able to form the imaging section 20 and the display section 30-equipped display device 40 independently from each other, as long as the imaging section 20 is able to image the object OB, the degrees of freedom are increased for the shape of the imaging section itself.

Note that the imaging section 20 and the display section 30 may exchange information using wired communication over a wired connection, or may exchange information using wireless communication over a wireless connection. The information exchanged between the imaging section 20 and the display section 30 is preferably digital information, in order to suppress image degradation caused by signal degradation with analogue signals. Examples of such digital information include digital signals, digital data, and image data representing the imaged image Im. For example, a display signal is an example of the information exchanged between the imaging section 20 and the display section 30, and a digital signal is preferably employed as this display signal. Moreover, the timing at which information is exchanged between the imaging section 20 and the display section 30 may be any out of a real-time timing, intermittent timing, or irregular timing. Exchanging digital information in real-time enables, for example, the observer OP to reference the image captured by the microscope 22 on the display section 30 in real time. An example of information exchanged at an intermittent timing is image data expressing an image captured by the microscope 22 in which the image data is exchanged in segments. Such an approach enables the amount of information in each exchange of digital data to be suppressed. An example of information exchanged at an irregular timing is an exchange of image data expressing a pre-captured image. In cases in which image data expressing a pre-captured image is exchanged, the image data may be held in advance in a non-illustrated recording device for this held image data to be read.

The information exchanged between the imaging section 20 and the display section 30 is not limited to digital display signals output from the imaging section 20 to the display section 30. For example, this information may include operation information of the imaging section 20. Examples of such operation information include information expressing an apparatus operational status such as, for example, at least one out of an optical magnification of the microscope 22 included in the imaging section 20, an electronic magnification of the camera 24, or a bitrate of the camera controller 26. The information exchanged between the imaging section 20 and the display section 30 may also include information output from the display section 30 to the imaging section 20. Examples of information output from the display section 30 to the imaging section 20 include command information expressing commands such as, for example, an optical magnification change instruction or the like for the microscope 22, an electrical magnification change instruction or the like for the camera 24, or a bitrate change instruction or the like for the camera controller 26.

In the following description, an inter-pupil direction of the observer OP when the ophthalmic system 10 is installed on a horizontal plane parallel with the ground is referred to as the "Y direction", a direction perpendicular to the horizontal plane on which the ophthalmic system 10 is installed is referred to as the "X direction", and a direction of light toward the observer OP when an image of the object OB is viewed by the observer OP is referred to as the "Z direction".

The ophthalmic system 10 according to the present exemplary embodiment will now be explained for an example of a case in which the observer OP views the object OB, which is the eye (examined eye) and the periphery of the examined eye, with the observer OP using both eyes (in binocular vision).

In cases in which the observer OP is viewing in binocular vision using both eyes, a conceivable case is one in which two images, one for the left eye and one for the right eye, being presented have a disparity due to parallax. In the present exemplary embodiment, the camera 24 is independently equipped with a left-eye camera 24L and a right-eye camera 24R in order to obtain two images with a disparity due to parallax. The left-eye camera 24L outputs a picture signal for the left eye to the camera controller 26, and the right-eye camera 24R outputs a picture signal for the right eye to the camera controller 26.

There are plural examples of methods to form an image for binocular vision on the display section 30 using the left-eye camera 24L and the right-eye camera 24R. These examples include cases in which a left-eye image and a right-eye image are independently formed as imaged images Im on the display section 30, and cases in which a left-eye image and a right-eye image are combined to form an imaged image Im on the display section 30.

Figure 2B:
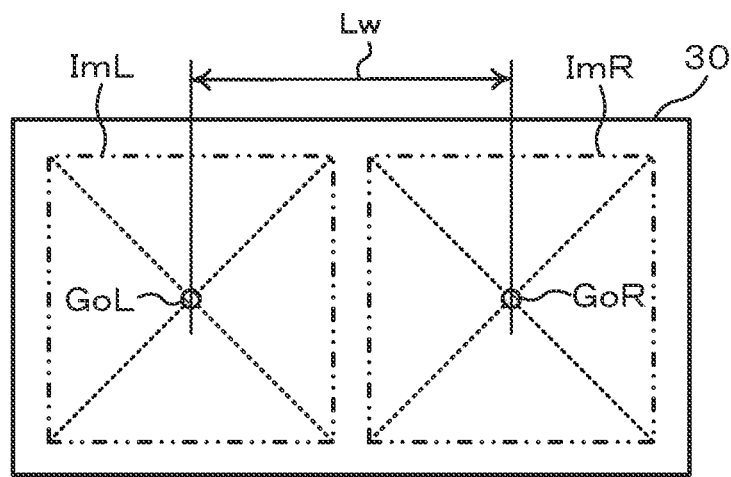
FIG. 2B is an illustration illustrating an example of a relationship between an imaging device and a display device for binocular vision according to an exemplary embodiment, illustrating a case in which in which combined display is performed.
Figure 2C:
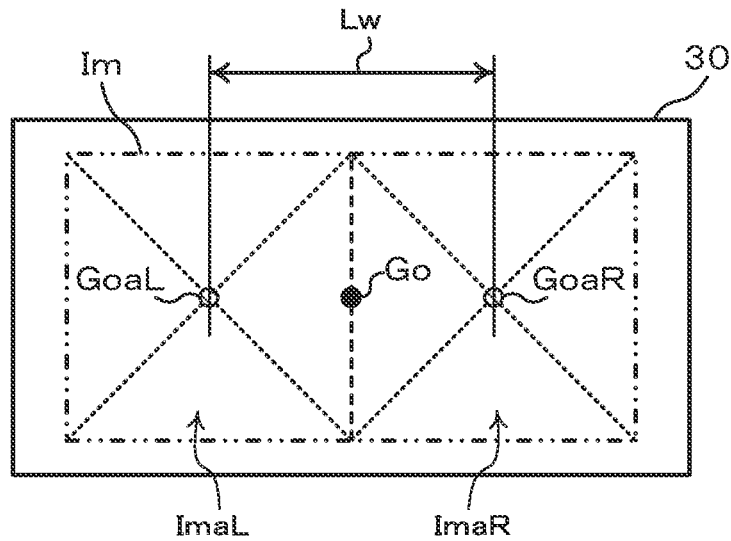
FIG. 2C is an illustration illustrating an example of a relationship between an imaging device and a display device for binocular vision according to an exemplary embodiment, illustrating a case in which in which single image display is performed.

FIG. 2A, FIG. 2B, and FIG. 2C illustrate examples of relationships between binocular vision imaged images and a display device.

FIG. 2A schematically illustrates a case in which a left-eye image and a right-eye image are respectively displayed on independent display sections. FIG. 2B schematically illustrates a case in which a left-eye image and a right-eye image are each displayed on a single display section. FIG. 2C schematically illustrates a case in which a single image incorporating both a left-eye image component and a right-eye image component is displayed on a single display section.

The example illustrated in FIG. 2A illustrates a case in which the display section 30 includes a left-eye display section 30L and a right-eye display section 30R. As a left-eye display function, an image from the camera 24L of the imaging section 20 is formed on the display section 30L as an imaged image ImL. The imaged image ImL reaches the left eye of the observer OP through a left-eye optical unit 42L and a reflection member 48. Similarly, as a right eye display function, an image from the camera 24R of the imaging section 20 is formed on the display section 30R as an imaged image ImR. The imaged image ImR reaches the right eye of the observer OP through a right-eye optical unit 42R and the reflection member 48.

In the example illustrated in FIG. 2A, respective positions of the left-eye imaged image ImL and the right-eye imaged image ImR are set such that a distance Lw between an image center GoL of the left-eye imaged image ImL and an image center GoR of the right-eye imaged image ImR corresponds to a pupil distance.

The example illustrated in FIG. 2B illustrates a case in which the imaged image ImL from the camera 24L and the imaged image ImR from the camera 24R are formed on the display section 30. In the example illustrated in FIG. 2B, respective positions of the left-eye imaged image ImL and the right-eye imaged image ImR are set such that a distance Lw between an image center GoL of the left-eye imaged image ImL and an image center GoR of the right-eye imaged image ImR corresponds to the pupil distance (for example the distance between the center of the pupil of the left eye of the observer OP and the center of the pupil of the right eye of the observer OP).

The example illustrated in FIG. 2C illustrates a case in which an imaged image Im combining an image component from the camera 24L and an image component from the camera 24R is formed on the display section 30. The image components referred to here are each information used to form part of the imaged image Im, and are, for example, image signals from the respective cameras. Namely, the imaged image ImL based on an image signal from the camera 24L and the imaged image ImR based on an image signal from the camera 24R are combined so as to be disposed at the left and right of one another to form the single imaged image Im. In the example illustrated in FIG. 2C, a left-eye imaged image corresponding to the left-eye imaged image ImL forms the left-eye imaged image predominantly in a left-eye area ImaL. The left-eye imaged image being predominantly in the left-eye area ImaL means the left-eye area ImaL is a predetermined region corresponding to part of the imaged image Im where the imaged image ImL based on the image signal from the camera 24L is arranged. For a corresponding right-eye imaged image ImR, a right-eye imaged image is formed as the right-eye imaged image predominantly in a right-eye area ImaR. In the example illustrated in FIG. 2C, an image center of the imaged image Im is at an image center Go; however the respective positions of the left-eye area ImaL and the right-eye area ImaR are set when forming the imaged image Im such that a distance Lw between a region center GoaL of the left-eye area ImaL predominantly for the left-eye imaged image ImL and a region center GoaR of the right-eye area ImaR predominantly for the right-eye imaged image ImR corresponds to the pupil distance.

Note that in the present exemplary embodiment, for ease of explanation, explanation is given regarding an example in which the ophthalmic system 10 is configured with an optical path for the right eye formed independently of an optical path for the left eye of the observer OP. Namely, in the ophthalmic system 10, an optical path for the left eye and an optical path for the right eye of the observer OP are formed so as to be independent of each other. For example, the imaging section 20 includes the right-eye camera 24R and the left-eye camera 24L, and the display section 30 includes the right-eye display section 30R and the left-eye display section 30L (see also FIG. 3A to FIG. 3C). The display device 40 includes the right eye display function to present the right-eye imaged image ImR to the right eye of the observer OP by being displayed on the display section 30R, and the left-eye display function to present the left-eye imaged image ImL to the left eye of the observer OP by being displayed on the left-eye display section 30L. Note that in the following explanation, the suffixes R and L will be omitted unless there is a need to discriminate between use with the right eye or the left eye.

Figure 3A:
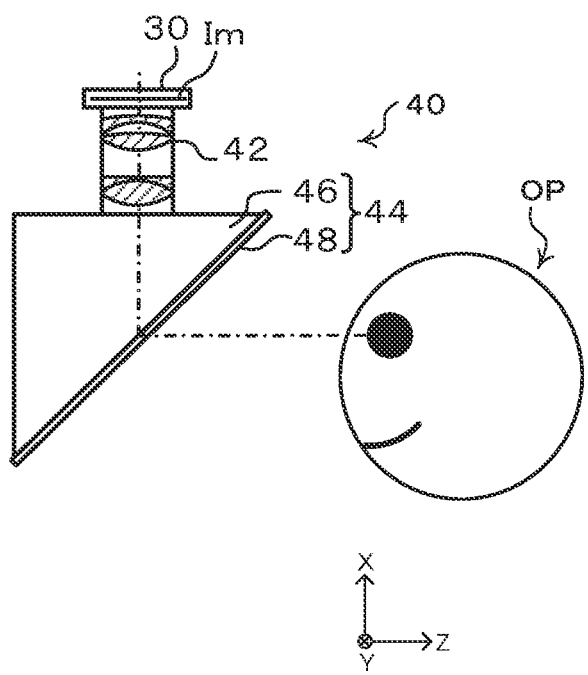
FIG. 3A is an illustration illustrating an example of configuration of a display device of an ophthalmic system according to an exemplary embodiment, illustrating the display device in side view.
Figure 3B:
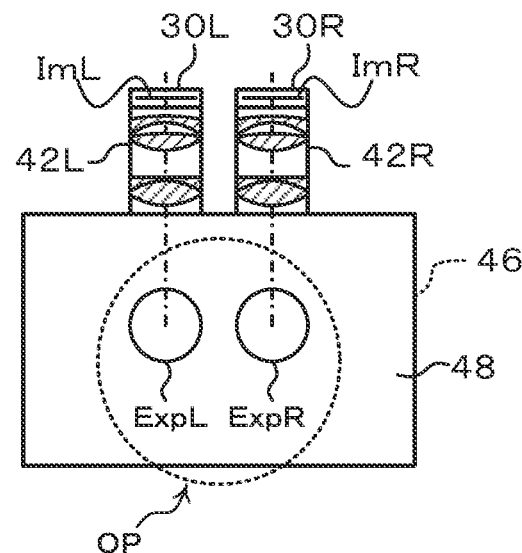
FIG. 3B is an illustration illustrating an example of configuration of a display device of an ophthalmic system according to an exemplary embodiment, illustrating the display device in front view.
Figure 3C:
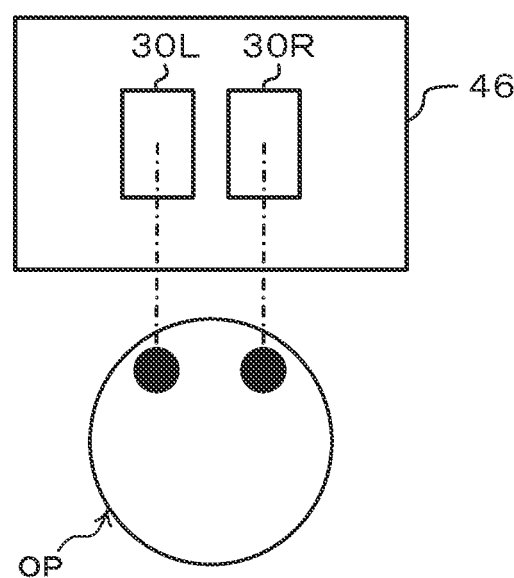
FIG. 3C is an illustration illustrating an example of configuration of a display device of an ophthalmic system according to an exemplary embodiment, illustrating the display device in plan view.

FIG. 3A, FIG. 3B, and FIG. 3C illustrate an example of a configuration of the display device 40. FIG. 3A illustrates a side view of the display device 40, FIG. 3B illustrates a front view, and FIG. 3C illustrates a plan view from above. Note that the example illustrated in FIGS. 3A to 3C is an example in which the reflection section 44 is a common reflection section (in this case, a single reflection section 44) employed for both the right eye and the left eye.

As illustrated in FIG. 3A to 3C, as the right-eye display function of display device 40, the imaged image ImR formed by the display section 30R as an image from the camera 24R is displayed in a space between the observer OP and the reflection section 44 for the right eye of the observer OP, through the right-eye optical unit 42R and the reflection member 48 of the reflection section 44. Moreover, as the left-eye display function of the display device 40, the imaged image ImL formed by the display section 30L as an image from the camera 24L is displayed in a space between the observer OP and the reflection section 44 for the left eye of the observer OP, through the left-eye optical unit 42L and the reflection member 48 of the reflection section 44.

As illustrated in FIG. 3B, the display device 40 forms a right-eye exit pupil (right pupil) ExpR and a left-eye exit pupil (left pupil) ExpL at the light exit side of the display device 40, namely, in front of the observer OP (for example in a space external to the display device 40 including the optical path between the eye of the observer OP and the reflection section 44). In the following description, the right-eye exit pupil ExpR and the left-eye exit pupil ExpL will be referred to collectively as "exit pupil Exp" unless there is a need to distinguish between left and right.

The ophthalmic system 10 of the present exemplary embodiment accordingly forms the image imaged by the right-eye camera 24R according to the disparity due to parallax present as the imaged image ImR on the display section 30R, and then displays this image through the optical unit 42R and the reflection member 48. Moreover, the image imaged by the left-eye camera 24L according to the disparity due to parallax present is formed as the imaged image ImL on the display section 30L, and then this image is displayed through the optical unit 42L and the reflection member 48. This thereby enables the object OB to be visually inspected as a three-dimensional image by the observer OP viewing the right-eye imaged image ImR and the left-eye imaged image ImL, which differ from each other according to the parallax disparity therebetween, by viewing the respective images in a prescribed space with the right eye or the left eye. In this manner, the ophthalmic system 10 of the present exemplary embodiment forms the exit pupil Exp described above in a space external to the display device 40 in a configuration enabling the observer OP to visually inspect the object OB as a three-dimensional image at a prescribed position even without a configuration including ocular lenses or 3D glasses.

Figure 4:
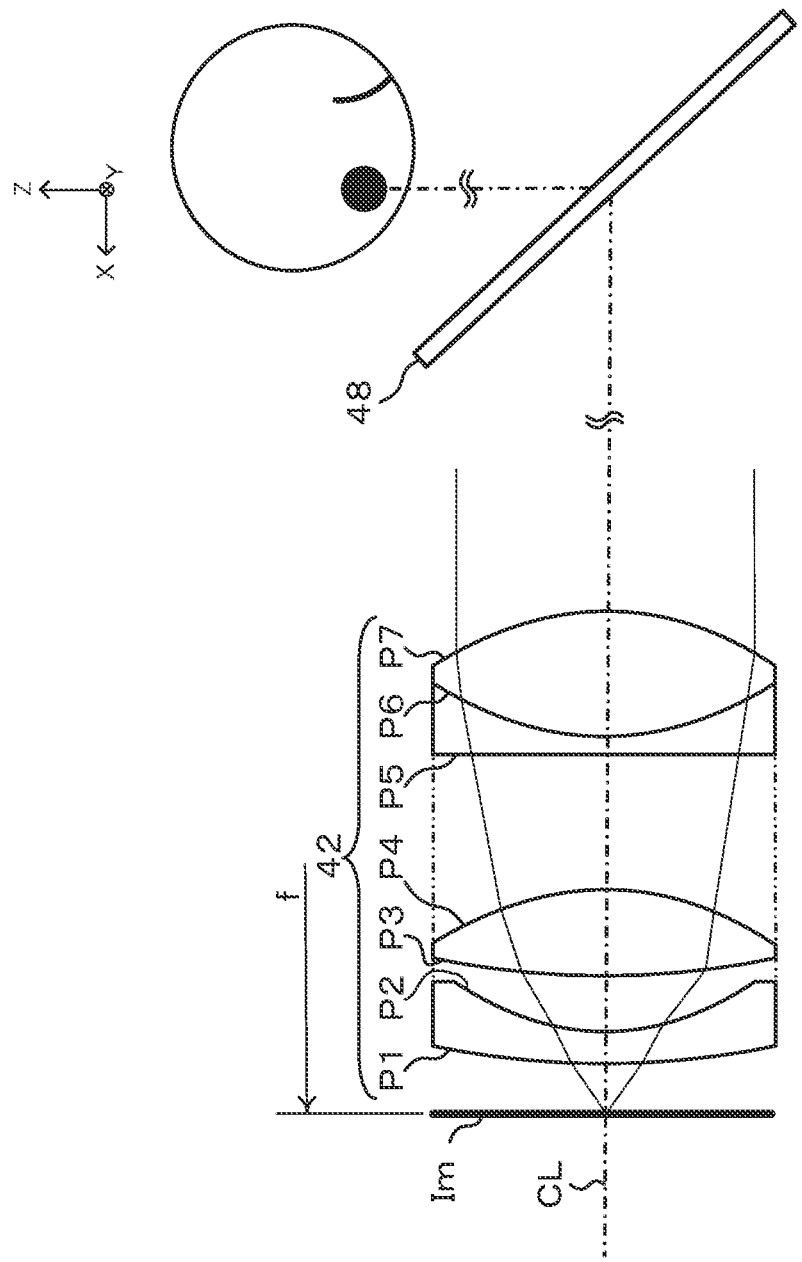
FIG. 4 is an illustration illustrating an example of configuration of an optical unit in an ophthalmic system according to an exemplary embodiment.

FIG. 4 illustrates an example of a configuration of the optical unit 42 that emits light toward the examined eye through the reflection member 48. Note that since the same configuration is employed for both the left-eye optical unit 42L and the right-eye optical unit 42R in the present exemplary embodiment, an explanation follows for an optical unit 42, and separate explanation of the left-eye optical unit 42L and the right-eye optical unit 42R will be omitted.

As illustrated in FIG. 4, the optical unit 42 includes a lens system formed with optical surfaces Nos. P1, P2, P3, P4, P5, P6, P7, P8, P9, P10, and P11, in this sequence from the imaged image Im. The optical surfaces are refraction surfaces where the refractive index of a medium on one side of the optical surface boundary is different from the refractive index of a medium on the other side thereof.

Specification values of the optical unit 42 are listed in the following Table 1.

In Table 1, Surface No. m corresponds to the Surface Nos. of the optical surfaces illustrated in FIG. 4. The radius of curvature r indicates a radius of curvature for each of the optical surfaces, the inter-surface distance d indicates a distance along the optical axis from one of the optical surfaces to the next optical surface, the refractive index nd indicates a refractive index with respect to D-lines, and dispersion vd indicates an Abbe number thereof. Although in the specification listed in Table 1 the units of "mm" are adopted for the radius of curvature r and for the inter-surface distance d, the optical unit 42 obtains equivalent optical properties by proportional enlargement or proportional shrinking thereof, and so there is no limitation to units of "mm", and another unit may be employed.

TABLE 1

| Surface No. m | Radius of Curvature r (mm) | Inter-Surface Distance d (mm) | Refractive Index nd | Dispersion vd | Effective diameter |
|---|---|---|---|---|---|
| 0 | ∞ | 11.4 | | | 61 |
| P1 | 191.626 | 6 | 1.7847 | 26.27 | 61 |
| P2 | 46.025 | 6.6 | | | 61 |
| P3 | 112.605 | 15.5 | 1.62041 | 60.25 | 61 |
| P4 | −48.973 | 25 | | | 61 |
| P5 | ∞ | 3 | 1.7195 | 35.25 | 61 |
| P6 | 49.28 | 22 | 1.62041 | 60.25 | 61 |
| P7 | −49.28 | 143 | | | 61 |
| reflective member | ∞ | — | | | 330 |
| reflective member | ∞ | 150 | | | 330 |
| pupil | | | | | |

Note that Table 1 relates to an example in which the optical surfaces have spherical shaped faces with an axis along an optical axis CL of the optical unit 42, however, the optical surfaces are not limited to being spherical shaped faces, and may be aspherical shaped faces.

The optical unit 42 is set such that the imaged image ImL formed by the display section 30 is positioned at the focal point position of focal length f on the display section 30 side. Light emitted from the optical unit 42 is thereby light of an afocal system, namely, parallel light. The parallel light emitted from the optical unit 42 reaches the eyes of the observer OP by passing through the reflection member 48 of the display device 40, forms an image on the retinas of the observer OP, and the imaged image Im is perceived by the observer OP.

The light emitted from the optical unit 42 is emitted toward the observer OP through the display device 40. However, this light is parallel light, and so the apparent size, namely the size of the imaged image Im viewed by the observer OP, does not change. In other words, the optical unit 42 emits parallel light so that the size of the imaged image Im does not change. By forming the optical unit 42 so as to emit parallel light in this manner, the apparent size does not change. What this means is, for example, that the size of an image does not change even if the distance between the reflection section 44 and the eyes of the observer OP changes.

By configuring the optical unit 42 such that the apparent size does not change, even if the observer OP were to change position (observation position of observer OP or eye position of the observer OP) in either a direction approaching the display device 40 or a direction away from the display device 40 such as, for example, the head of the observer OP moving forward or backward along the optical axis direction, the observed size of the imaged image Im would not change. The observer OP is thereby permitted to undertake a larger change in posture than in a case in which there is a set posture to view the imaged image Im according to the size of the imaged image Im.

Since it is difficult in the optical unit 42 to maximize the pupil and angle of view using a single lens group, two or more lens groups are preferably formed. However, there is an increased possibility of flare increasing as the number of lens groups configuring the optical unit 42 increases.

Accordingly, in the present exemplary embodiment a lens configuration of four elements in three groups is adopted as the optimal lens configuration capable of enlarging the pupil and enlarging the observable image range while suppressing an increase in the effective diameter. In the example illustrated in FIG. 4, a first lens group is configured by a negative power meniscus lens formed by the optical surface Nos. P1, P2. A second lens group is a positive power convex lens formed by the optical surface Nos. P3, P4. A third lens group is a stuck-together lens group produced by sticking together a negative power meniscus lens and a positive power convex lens, and is formed by the optical surface Nos. P5, P6, and P7.

The first lens group and the second lens group preferably have a positive composite focal point. The third lens group is preferably a stuck-together lens group. This is in order to obtain a function that corrects axial chromatic aberration. Moreover, the Abbe number of the convex lens of the third group is preferably higher than that of the concave lens therein. Regarding the first lens group and the second lens group, in order to obtain a function that corrects chromatic aberration of magnification, a distance between the first lens group and the second lens group is preferably shorter than the distance between the second lens group and the third lens group.

Moreover, the optical unit 42 is preferably formed such that the first incident surface for incident light (the optical surface No. P1 illustrated in FIG. 4) is a refraction surface configured by a face concave on the light incident side. The optical unit 42 suppresses attenuation of peripheral light by bringing the main light rays of the incident light close to parallel to the optical axis. Fluctuations in magnification are also suppressed when defocused.

Moreover, the optical unit 42 is formed such that the exit pupil Exp is positioned at a position at or beyond the outermost surface on the light exit side of the optical unit 42. In cases in which the exit pupil Exp is positioned at a position at or beyond the outermost surface on the light exit side of the optical unit 42, the left-eye optical unit 42L is suppressed from becoming more bulky. In the example illustrated in FIG. 4, the exit pupil Exp is formed so as to be positioned at a position at or beyond the last lens as light is being emitted, namely the lens including the optical surface No. P7. A configuration may also be adopted in which the exit pupil Exp is positioned at a position at or beyond a nearest lens to the reflection section 44 that is positioned at the side of light exit from the optical unit 42.

The optical unit 42 is an example of a case in which the exit pupil Exp is positioned at the outermost surface on the exit side (on a flat plane orthogonal to the optical axis CL and including the point of intersection between the optical surface No. P7 and the optical axis CL). However, the position of the exit pupil is not limited to being at the outermost surface on the exit side of the optical unit 42, and the optical unit 42 is suppressed from becoming more bulky even in cases in which the exit pupil is positioned in the vicinity of the outermost surface.

Forming the exit pupil Exp so as to be positioned at a position at or beyond the outermost surface on the exit side of the optical unit 42 in this manner enables the exit pupil to be formed with a size corresponding to the lens diameter of the optical unit 42.

Note that a light-suppressing portion functioning as a partition may be provided between the right-eye optical unit 42R and the left-eye optical unit 42L in order to suppress light from straying between one and the other of the right-eye optical unit 42R and the left-eye optical unit 42L. Such a light-suppressing portion preferably includes a light absorbing member.

Moreover, when the observer OP is viewing with both eyes with binocular vision or the like, preferably the left and right images are displayed at a separation from each other corresponding to the pupil distance (PD) between the two eyes of the observer OP. Thus the respective lens diameters of the left-eye optical unit 42L and the right-eye optical unit 42R are preferably not greater than the pupil distance PD. For example, taking an observer with a pupil distance PD of 65 mm as the standard, the respective lens diameters are preferably not greater than 65 mm. Moreover for the observer OP with a pupil distance PD of 65 mm, when forming the imaged image Im with the display section 30 that has a pixel size of at least 15 μm, the focal length f of the optical unit 42 is preferably from 25 mm to 100 mm.

As illustrated in FIG. 1, the reflection section 44 includes the case 46 and the reflection member 48. The optical unit 42 is attached to the case 46, and the light that has been emitted from the optical unit 42 is introduced into the case 46. Moreover, the reflection member 48 is attached to the case 46 at the light exit side of the optical unit 42 such that the incident face (reflection surface) thereof reflects light along a direction intersecting with the emitting optical axis (optical axis of emitted light) of the optical unit 42 (i.e. in a direction toward the observer OP). The reflection section 44 reflects the light that has been emitted from the optical unit 42 along a direction intersecting with the emitting optical axis of the optical unit 42, and forms an exit pupil at a position on the reflection side having a conjugate relationship to the exit pupil of the optical unit 42. Namely, the reflection section 44 relays the exit pupil of the optical unit 42 by re-forming the exit pupil at the reflection side, i.e. in the direction toward the observer OP.

As an example of the reflection member 48, in the present exemplary embodiment an optical image forming element 48A is employed to form an image of the same magnification by multiple reflections using plural reflection surfaces.

For example, the optical image forming element 48A is equipped with plural reflection members configured by plural reflection surfaces in stacked layers, with light incident to one stacked-layer end face being reflected by the reflection surfaces and emitted from the other stacked-layer end face. The plural reflection members are arranged such that the reflection surface of one reflection member and the reflection surface of another reflection member are oriented in intersecting directions, and such that the light emitted from a stacked-layer end face of one reflection member is incident to a stacked-layer end face of the other reflection member.

Namely, the incident light incident on the optical image forming element 48A is reflected by a first reflection surface from out of the plural reflection surfaces, the reflected light is then reflected by a second reflection surface and then emitted from the optical image forming element 48A. The first reflection surface and the second reflection surface are arranged in the optical image forming element 48A such that the reflection surfaces thereof are oriented in intersecting (orthogonal) directions. Thus in cases in which the first reflection surface and the second reflection surface are orthogonally arranged in plan view, the incident light to the optical image forming element 48A and the light emitted from the optical image forming element 48A are parallel when the optical image forming element 48A is viewed in plan view. Thus plural light points that are actual points on the incident side of the optical image forming element 48A are converged on the exit side of the optical image forming element 48A and formed as an image of virtual points. Thus in the present exemplary embodiment, the reflection section 44 re-forms the exit pupil at a position having a conjugate relationship to the exit pupil of the optical unit 42.

Note that the optical image forming element 48A can be treated as being a recursive element, or more precisely as being a recursive pass-through element. Recursive reflection is reflecting light in an opposite direction to the direction of light incident to the element using plural orthogonal reflection surfaces. However, the optical image forming element 48A of the present exemplary embodiment has the property of letting incident light pass through to a face on the opposite side to the incident face, and emitting the light with changed direction when doing so. Light rays are replicated with plane symmetry with respect to a flat plane orthogonal to a normal to the optical image forming element. In this action, when the optical image forming element performs spatial replication, the progression direction of the light rays is not changed in relation to the perpendicular direction of the optical image forming element 48A, and corresponds to a recursive action, and so the optical image forming element 48A can be thought of as being a recursive pass-through element. Employing the recursive pass-through element provided with plural reflection surfaces in this manner enables light attenuation to be suppressed while effectively utilizing the light emitted from the optical unit 42.

Another example of the optical image forming element 48A is a light control panel including plural intersecting reflection surfaces as a unit optical system, with plural of these unit optical systems arrayed along the directions of a flat plane intersecting with the plural reflection surfaces. More specifically, a light control panel is formed by arraying plural unit optical systems configured from two substantially mutually orthogonal mirror faces that are substantially perpendicular to a prescribed flat plane, such as for example, two-face corner reflectors.

Figure 5:
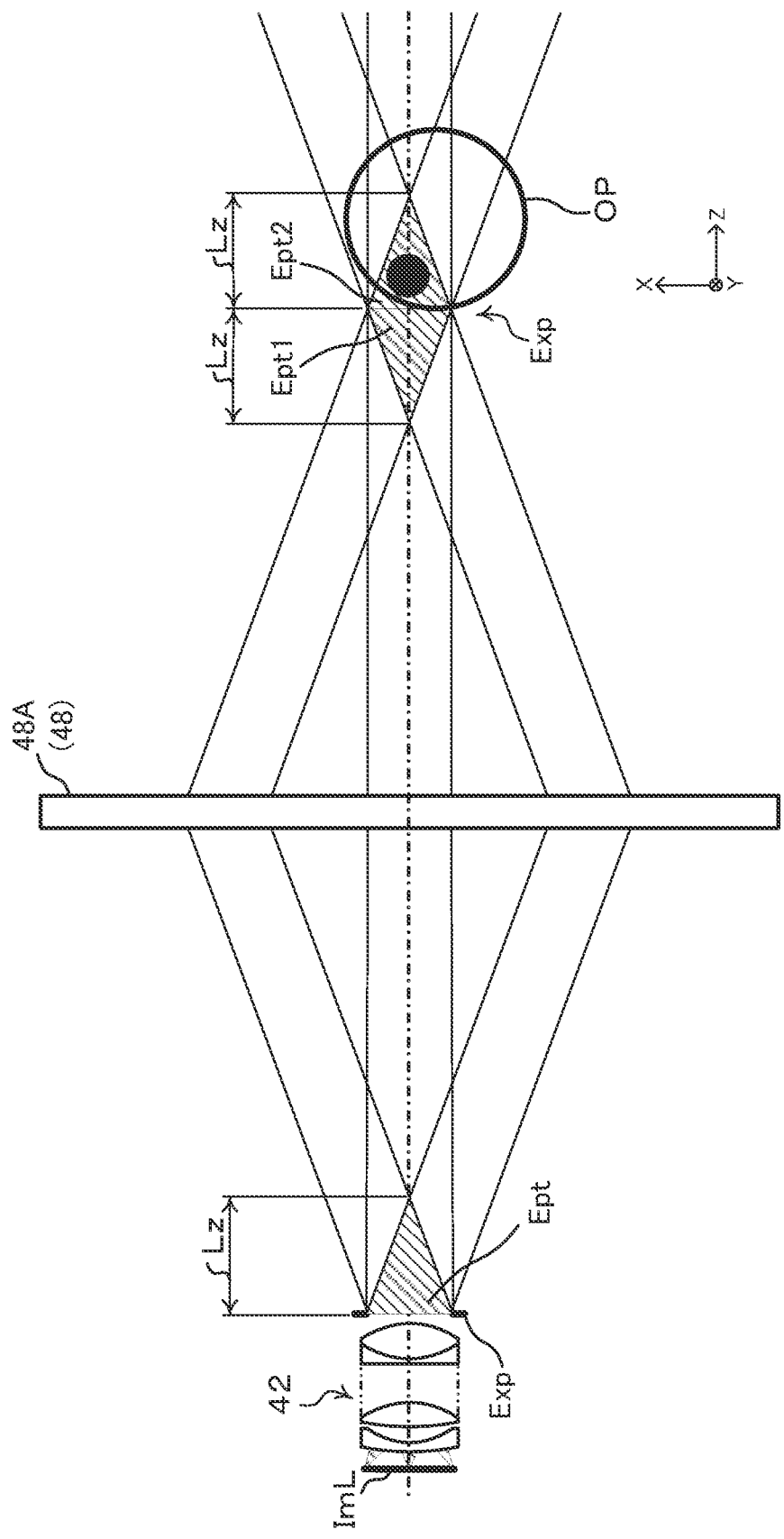
FIG. 5 is an illustration illustrating an example of optical paths in a display device included in an ophthalmic system according to an exemplary embodiment.

FIG. 5 illustrates an example of optical paths in the display device 40.

As illustrated in FIG. 5, each of the pixels of the imaged image Im of the object OB from the display section 30 emits parallel light rays from the exit pupil Exp of the optical unit 42, and a pupil is re-formed by the exit pupil being replicated and formed by the optical image forming element 48A. In the display device 40, the exit pupil Exp of the optical unit 42 forms an exit pupil Exp at a position on the outermost surface on the light exit side of the optical unit 42, so as to form eye points Ept. The eye points Ept are ranges where light emitted from the optical unit 42 encompassing all angles of view is visible. In the example illustrated in FIG. 5, each of the eye points Ept is formed over a range from the exit pupil Exp spanning up to a distance Lz therefrom in the optical axis direction.

The pupil is re-formed by being replicated with the optical image forming element 48A and forming the conjugate exit pupil Exp. Thus an eye point Ept1 is formed conjugate to an eye point Ept on the light exit side of the optical unit 42, and an eye point Ept2 is also formed further along the light progression direction. This results in eye points where the observer OP is able to observe at the eye point Ept1 and the eye point Ept2, enabling eye points to be formed over twice the range of that of the eye point Ept. Namely, forming the exit pupil Exp in space enables eye points to be formed at both the inside of the exit pupil Exp (this being the eye point Ept1 in the direction away from the observer OP) and at the outside of the exit pupil Exp (this being the eye point Ept2 in the direction heading from the exit pupil Exp toward the observer OP), i.e. eye points can be formed over twice the range of an ordinary observation device having an eye point is formed at the outside of the exit pupil Exp. This accordingly enables the moveable range of the position of the eyes of the observer OP, namely the position of the head of the observer OP, to be expanded to twice the range. The permissible range defined for the position of the head of the observer OP can thereby be expanded, enabling an increase in the degrees of freedom for setting the position of the head of the observer OP.

In the example illustrated in FIG. 5, the optical paths of the display device 40 are illustrated for a flat plane containing the optical axis CL, and a viewable range encompassing all angles of view of light emitted from the optical unit 42 is illustrated by the eye point Ept. However, the light emitted from the optical unit 42 is composed of light rays having rotational symmetry about an axis of the optical axis CL. Thus the eye point Ept described above can be thought of as being an eye box of a substantially conical shaped region with an axis along the optical axis CL.

Moreover, the present exemplary embodiment is configured such that the position of the exit pupil Exp is positioned on the outermost surface on the light exit side of the optical unit 42. Namely, the exit pupil Exp of the display device 40 is formed as the right-eye exit pupil and as the left-eye exit pupil. This accordingly enables the exit pupils of the optical unit 42 to be formed with a size corresponding to the lens diameter of the optical unit 42, enabling the diameters of both the right-eye exit pupil and the left-eye exit pupil to be expanded to a size corresponding to the lens diameter in the optical unit 42. By positioning each of the eyes of the observer OP in the prescribed space and inside these exit pupils, the observer OP is able to visually inspect the imaged image ImL for the left-eye of the observer OP and the imaged image ImR for the right-eye of the observer OP. The ophthalmic system 10 of the present exemplary embodiment accordingly does not need a mechanism to adjust the pupil distance PD, such as a mechanism installed in a binocular view microscope of related art.

As described above, an eye box configured by the eye point Ept1 and the eye point Ept2 conjugate to the eye point Ept in the optical unit 42 expands the observable range of the observer OP, and thus expands the moveable range for the position of the eyes of the observer OP, namely for the position of the head of the observer OP.

Note that as long as the object is observable, the head of the observer OP may be closer to the display device 40, and in particular to the reflection section 44. When the head of the observer OP has been moved closer to the reflection section 44, the likelihood increases that the head of the observer OP might contact the reflection section 44.

The reflection section 44 is therefore preferably set an appropriate distance from the eye box. Specifically, the position of a re-formed pupil replicated by the reflection member 48 (optical image forming element 48A) preferably satisfies conditions of equation $$d_0 > (1 + \tan\theta / \tan\Psi)^2 \cdot (\varphi / 2 \tan\theta)$$

Note that $\Psi$ is an angle formed between the installed reflection member 48 and the optical axis Cl, $\theta$ is an angle half the field of view angle, $\varphi$ is the pupil diameter, and do is the distance from the pupil to the point of intersection between the optical axis CL and the reflection member 48.

Specifically, in a case in which the reflection member 48 re-forms the pupil at the same size (same magnification of 1:1), and in the desired installation the distance between the pupil and the reflection member 48 is do, the distance between the exit pupil of the optical unit 42 and the reflection member 48 should be set to do. In such cases, ranges of the angle $\theta$ and the angle $\Psi$ are the respective ranges of $0° < \theta < 90°$ and $0° < \Psi < 90°$.

Next, the position of the pupil re-formed according to the conditions of the above equation above will be considered with reference to the relationship between the reflection member 48 (optical image forming element 48A) and the pupil.

Figure 6:
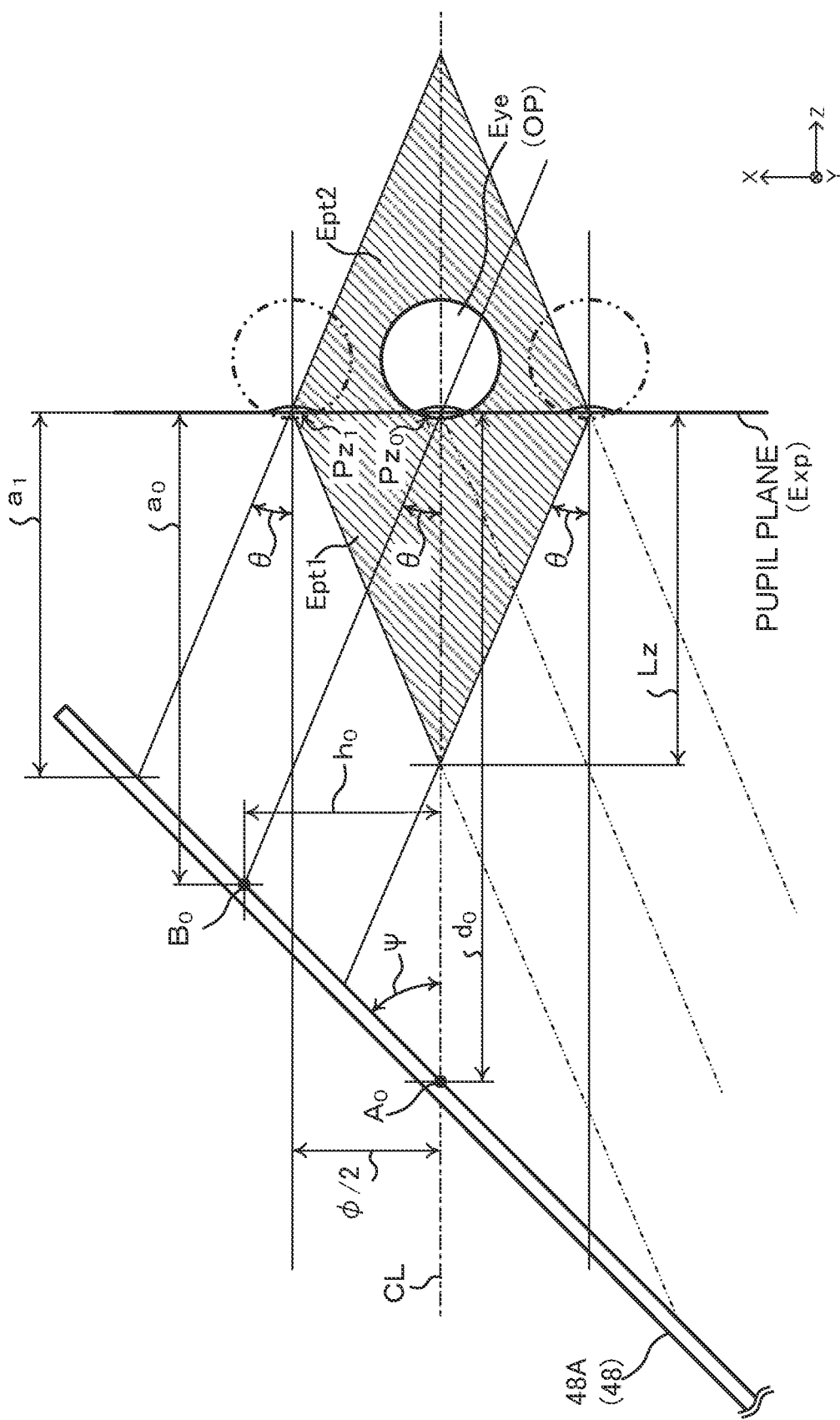
FIG. 6 is an illustration illustrating an example of optical paths related to a pupil and to a reflection member according to an exemplary embodiment.

FIG. 6 illustrates an example of optical paths related to the reflection member 48 and the pupil.

As illustrated in FIG. 6, a pupil is re-formed by replicating with the reflection member 48 and forming the conjugate exit pupil Exp. A pupil plane of the exit pupil Exp is illustrated in the example FIG. 6. The example illustrated in FIG. 6 illustrates a case in which the reflection member 48 is installed such that the angle $\Psi$ is an angle formed between the reflection member 48 and the optical axis CL.

In this case, the field of view half-angle is angle $\theta$, the diameter of the pupil is denoted pupil diameter $\varphi$, and when the pupil of an eye Eye of the observer OP is positioned at the pupil center (at the position $Pz_0$ in FIG. 6), the point of intersection between the optical axis CL and the reflection member 48 is point $A_0$ and a point of intersection between a maximum angle of view $\theta$ and the reflection member 48 is point $B_0$. The Z direction distance from the pupil plane to the point $A_0$ is distance $d_0$, and the Z direction distance from the pupil plane to the point $B_0$ is distance $a_0$.

A distance $h_0$ from the point $B_0$ to the optical axis CL can be expressed by Equation (1) below in terms of the angle $\Psi$.

$$d_0 = (d_0 - a_0)\tan\Psi \qquad \text{Equation (1)}$$

Expressed in terms of the angle $\theta$ produces Equation (2) below.

$$h_0 = a_0 \cdot \tan\theta \qquad \text{Equation (2)}$$

From Equation (1) and Equation (2), the distance $d_0$ from the pupil to point $A_0$ can be expressed by Equation (3) below.

$$d_0 = (1 + \tan\theta/\tan\Psi) \cdot a_0 \quad \text{Equation (3)}$$

When the pupil is placed at a pupil upper edge position $Pz_1$, a distance $a_1$ from the pupil plane to the nearest position can be expressed in terms of the distance $a_0$ by Equation (4) below.

$$a_1 = a_0 - \varphi/2 \tan\Psi \quad \text{Equation (4)}$$

Equation (4) can be rewritten in terms of the distance $a_0$ and expressed as Equation (5) below.

$$a_0 = a_1 + \varphi/2 \tan\Psi \quad \text{Equation (5)}$$

Accordingly, by substituting Equation (5) into Equation (3), the relationship between the distance $d_0$ from the pupil plane to the point $A_0$ and the distance $a_1$ from the pupil plane to the nearest position can be expressed by Equation (6) below.

$$d_0 = (1 + \tan\theta/\tan\Psi) \cdot (a_1 + \varphi/2 \tan\Psi) \quad \text{Equation (6)}$$

Next, explanation follows regarding a limit value (front limit value) of the eye box on the reflection member 48 side.

The limit value (front limit value) of the eye box on the reflection member 48 side is a distance Lz along the Z axial direction (optical axis direction) from the exit pupil Exp. The distance Lz can accordingly be expressed by Equation (7) below in terms of the half-angle of the field of view, namely angle $\theta$, and the pupil diameter, namely pupil diameter $\varphi$.

$$Lz = \varphi/2 \tan\theta \quad \text{Equation (7)}$$

Note that as described above, the position of the eye of the observer OP may be moved forward or backward in the optical axis direction within a distance Lz range from the pupil plane at the center. In cases in which the above-mentioned distance $a_1$ from the pupil plane to the nearest position is the same as the distance Lz or shorter than the distance Lz ($a_1 \leq Lz$), the head of the observer OP might approach and contact the reflection member 48.

Accordingly, the distance $a_1$ from the pupil plane to the nearest position is preferably set longer than the distance Lz, as expressed by Equation (8) below.

$$a_1 > Lz \quad \text{Equation (8)}$$

Next, explanation follows regarding a relationship between the angle $\theta$ for the half-angle of the field of view and the pupil diameter $\varphi$, and the distance Lz.

The distance Lz is determined by the angle $\theta$ for the half-angle of the field of view and the pupil diameter $\varphi$. This thereby enables a range to be determined for the distance $a_1$ from the pupil plane to nearest position and a range to be determined for the distance $d_0$ from the pupil plane to the nearest position. Table 2 below illustrates an example of positional relationships between the reflection member 48 and the pupil.

TABLE 2

| | | | | when $a_1$ = Lz | |
| $\theta$ (deg) | $\varphi/2$ (mm) | $\Psi$ (deg) | Lz (mm) | $a_1$ (mm) | $d_0$ (mm) |
| --- | --- | --- | --- | --- | --- |
| 18 | 15 | 45 | 46.1653 | 46.1653 | 81.039 |
| 18 | 25 | 45 | 76.9421 | 76.9421 | 135.065 |
| 24 | 15 | 45 | 33.6906 | 33.6906 | 70.369 |
| 24 | 25 | 30 | 56.1509 | 56.1509 | 176.146 |

TABLE 2-continued

| | | | | when $a_1$ = Lz | |
| $\theta$ (deg) | $\varphi/2$ (mm) | $\Psi$ (deg) | Lz (mm) | $a_1$ (mm) | $d_0$ (mm) |
| --- | --- | --- | --- | --- | --- |
| 24 | 25 | 45 | 56.1509 | 56.1509 | 117.282 |
| 24 | 25 | 60 | 56.1509 | 56.1509 | 88.7287 |

Note that although Table 2 illustrates examples for a case with the condition $a_1 = Lz$, in cases in which $a_1 > Lz$ a range can be determined for the distance $a_1$ and the distance $d_0$ can be determined using Equation (9) below and from Equation (6) above.

$$d_0 > (1 + \tan\theta/\tan\Psi)^2 \cdot (\varphi/2 \tan\theta) \quad \text{Equation (9)}$$

Namely, in cases in which in which $a_1 > Lz$, since $Lz = (\varphi/2 \tan\theta)$, Equation (6) can be expanded as follows.

$$\begin{aligned}
d0 &> (1 + \tan\theta/\tan\Psi) \cdot (a_1 + \varphi/2\tan\Psi) = (1 + \tan\theta/\tan\Psi) \cdot \\
&\quad \{(\varphi/2\tan\theta) + (\varphi/2\tan\Psi)\} \\
&= (1 + \tan\theta/\tan\Psi) \cdot \\
&\quad (1 + \tan\theta/\tan\Psi) \cdot \\
&\quad (\varphi/2\tan\theta) \\
&= (1 + \tan\theta/\tan\Psi)^2 \cdot \\
&\quad (\varphi/2\tan\theta)
\end{aligned}$$

Next, more specific explanation follows regarding an example of a case in which the reflection member 48 is set such that the angle $\Psi$ formed between the reflection member 48 and the optical axis CL is 45°.

Equation (1) above can be expressed using Equation (10).

$$h_0 = d_0 - a_0 \quad \text{Equation (10)}$$

The Equation (3) expressing the distance $d_0$ from the pupil to the point $A_0$ can be expressed by Equation (11) below by using Equation (10) and Equation (2) based on the angle $\theta$.

$$d_0 = (1 + \tan\theta) \cdot a_0 \quad \text{Equation (11)}$$

Equation (4) can be expressed by Equation (12) below, and Equation (5) can be expressed by Equation (13) below.

$$a_1 = a_0 - \varphi/2 \quad \text{Equation (12)}$$

$$a_0 = a_1 + \varphi/2 \quad \text{Equation (13)}$$

Equation (6) above can therefore be simplified to Equation (14) below.

$$d_0 = (1 + \tan\theta) \cdot (a_1 + \varphi/2) \quad \text{Equation (14)}$$

Next, explanation follows regarding ranges for the distance $a_1$ and the distance do when the angle $\Psi$ is set to 45°. An example of positional relationships between the reflection member 48 and the pupil is illustrated in Table 3 below.

TABLE 3

| | | | | when $a_1$ = Lz | |
| $\theta$ (deg) | $\tan\theta$ | $\varphi/2$ (mm) | Lz (mm) | $a_1$ (mm) | $d_0$ (mm) |
| --- | --- | --- | --- | --- | --- |
| 18 | 0.32492 | 15 | 46.1653 | 46.1653 | 81.039 |
| 24 | 0.445229 | 15 | 33.6906 | 33.6906 | 70.369 |
| 18 | 0.32492 | 25 | 76.9421 | 76.9421 | 135.065 |
| 24 | 0.445229 | 25 | 56.1509 | 56.1509 | 117.2816 |

Note that although Table 3 illustrates examples for a case with the condition $a_1 = Lz$, in cases in which $a_1 > Lz$, ranges for the distance $a_1$ and the distance $d_0$ can be determined using Equation (15) below based on Equation (14).

$$d_0 > (1+\tan\theta)^2 \cdot (\varphi/2 \tan\theta) \qquad \text{Equation (15)}$$

The above example is an example in which the half-angle of the field of view, namely angle $\theta = 24°$, and the pupil diameter $\varphi = 50$. Since $d_0 = 150$, the relationship $a_1 > Lz$ is satisfied.

Setting the position of the pupil replicated and re-formed by the reflection member 48 so as to satisfy the conditions of the above equation enables the permitted range determined for the position of the head of the observer OP to be expanded while suppressing contact of the head of the observer OP with the reflection member 48. This enables an increase in the degrees of freedom when setting the position of the head of the observer OP.

The size, namely the diameter, of the exit pupil Exp is limited by the lens diameter of the optical unit 42. In cases in which there is a demand to make the size of the exit pupils Exp larger to expand the inspectable range of the observer OP, the lens diameter of the optical unit 42 can be made larger than the pupil distance PD, and portions of the optical unit 42 that would overlap with each other may be machined off from at least one out of the left-eye or right-eye sections of the optical unit 42.

There are cases in which the observer OP may wish to shift gaze when viewing the imaged image Im of the object OB during observation. In such cases, configuration may be made such that the optical axis of the imaged image Im of the object OB for display to the observer OP is adjustable. For example, the reflection member 48 may be formed so as to be rotatable by an actuator about an axis in a direction intersecting the emitting optical axis of the optical unit 42. In cases in which the optical axis of light emitted from the reflection member 48 is set so as to run in a horizontal direction parallel to the floor on which the ophthalmic system 10 is installed (for example the Z direction), rotating the reflection member 48 by a prescribed angle in a counterclockwise direction rotates the optical axis of the light emitted from the reflection member 48 by an angle twice as large in the counterclockwise direction. Accordingly, the gaze direction of the observer OP viewing the imaged image Im can be shifted downward from the horizontal direction. On the other hand, rotating the reflection member 48 in the opposite direction enables the gaze direction of the observer OP viewing the imaged image Im to be shifted upward from the horizontal direction.

In cases in which the observer OP has farsightedness or myopia, this makes it difficult to focus on the imaged image Im of the object OB being viewed using the ophthalmic system 10, namely, the imaged image Im appears blurred when viewed. In such cases, a diopter adjustment mechanism may be provided to adjust the diopters to match the condition of the eyes of the observer OP. An example of a diopter adjustment mechanism is a configuration formed so convert parallel light emitted toward the observer OP so as to be emitted as divergent light or converging light. For example, in order to convert parallel light emitted toward the observer OP so as to be emitted as divergent light or converging light, a diopter adjustment mechanism may be formed so as to be capable of changing the position in the optical axis direction of at least one out of the display section 30 forming the imaged image Im or the optical unit 42. Namely, such a diopter adjustment mechanism may be configured including an actuator or the like capable of moving by at least one out of moving the position of the display section 30 forming the imaged image Im or moving the position of the optical unit 42. Note that changing the position of the optical unit 42 also changes the position of the exit pupils, and so the diopter adjustment mechanism preferably includes configuration to change the position of the display section 30. Cases in which the light emitted toward the observer OP has been converted from parallel light to divergent light (by moving the display section 30 and the optical unit 42 away from each other) are cases of adjustment in diopters for myopia, whereas moving the display section 30 closer to the optical unit 42 are cases of adjustment in diopters for farsightedness.

However, in cases in which the observer OP views through both eyes (with binocular vision) the eye (examined eye) and the periphery of the examined eye serving as the object OB, preferably an image can presented to the observer OP under prescribed conditions in order to suppress discomfort of the observer OP that may lead to eye strain These prescribed conditions are presenting an image such that the convergence angle arising is viewable with both eyes. An example of such prescribed conditions is a first condition that an angle formed between the gaze axis (gaze direction optical axis) of the left eye and the gaze axis of the right eye when looking at the focal point position is an ideal convergence angle, and a second condition that images having respective parallax disparity for binocular vision are observed with both eyes.

Thus so as to satisfy such prescribed conditions, the ophthalmic system 10 according to the present exemplary embodiment employs the optical properties of the reflection member 48 (optical image forming element 48A) to display the imaged images Im to the two eyes of the observer OP so as to cause the convergence angle to arise.

For example, although the reflection member 48 is an element that lets light pass through, in cases in which the optical image forming element 48A described above is employed, as a result of the structure of the optical image forming element 48A, light rays passing through the optical image forming element 48A maintained their angle in one direction, and are inverted in angle in another direction orthogonal to the one direction. Namely, in the example illustrated in FIG. 5, the angle of light rays in the x axis direction as viewed by the observer OP is maintained and the angle of the light rays in the y axis direction is inverted.

In the present exemplary embodiment, the optical properties that arise from the structure of the reflection member 48, which are that light rays passing through the reflection member 48 either maintain angle or are inverted in angle, are employed to give an angle to the optical path of the light rays in the y axis direction, i.e. in the inter-pupil direction, and to display the images Im such that a convergence angle is caused to arise between the two eyes of the observer OP.

Figure 7B:
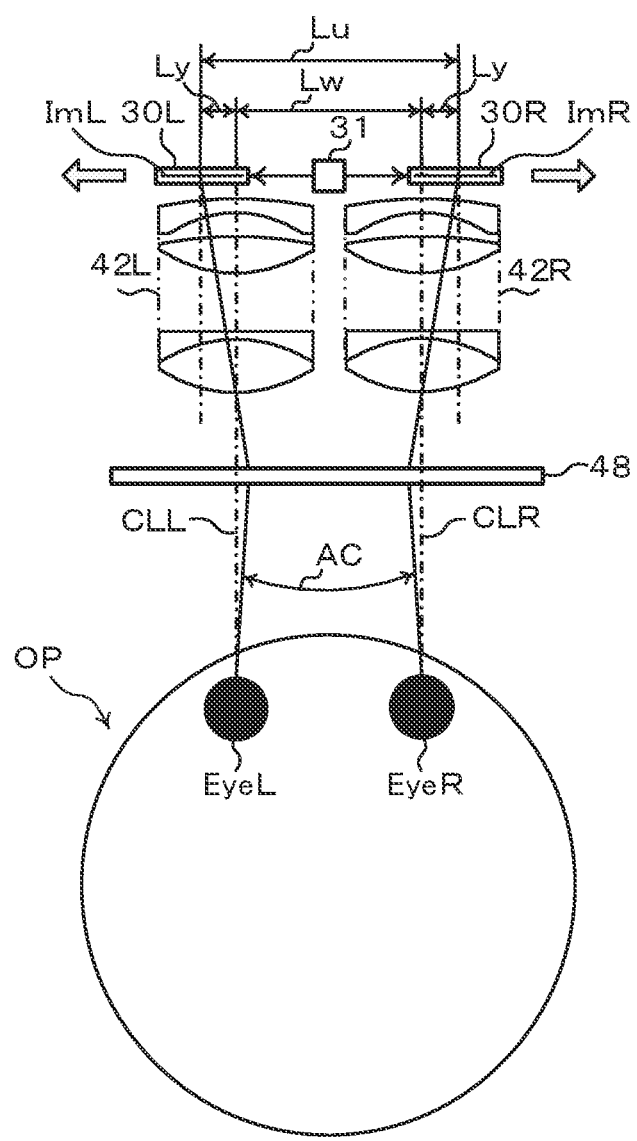
FIG. 7B is a schematic diagram illustrating an example of optical paths in a display device according to an exemplary embodiment, and illustrates a display device that causes a convergence angle to arise.

FIG. 7A and FIG. 7B schematically illustrates an example of optical paths of the images Im to cause a convergence angle to arise between the two eyes of the observer OP FIG. 7A illustrates a case in which an optical axis CLL of the left-eye optical unit 42L and an optical axis CLR of the right-eye optical unit 42R are parallel to each other, and the left-eye optical unit 42L and the right-eye optical unit 42R are disposed at a separation of the distance Lw corresponding to the pupil distance of the observer OP.

In FIG. 7A, the center of the imaged image ImL is positioned at an intersection position between the left-eye optical axis CLL and the display section 30L. The center of the imaged image ImR is positioned at an intersection position between the right-eye optical axis CLR and the display section 30R. As illustrated in FIG. 7A, the optical paths when the observer OP views the imaged image Im with both eyes are parallel to each other. Namely, the viewing optical path of the left eye EyeL of the observer OP is directed toward the center of the imaged image ImL and the viewing optical path of the right eye EyeR is directed toward the center of the imaged image ImR, and are parallel to each other. This results in a state in which it is difficult to form a convergence angle between the two eyes of the observer OP.

On the other hand, FIG. 7B illustrates an example of the display device 40 of the ophthalmic system 10 according to the present exemplary embodiment. In the example illustrated in FIG. 7B, the center of the imaged image ImL is disposed at a position away from the optical axis CLL of the left-eye optical unit 42L, and the center of the imaged image ImR is disposed at a position away from the optical axis CLR of the right-eye optical unit 42R. In the present exemplary embodiment, the left-eye display section 30L and the right-eye display section 30R are formed capable of moving in the y axis direction, i.e. the inter-pupil direction of the observer OP by using a convergence angle adjustment mechanism 31 for the display section. The left-eye display section 30L and the right-eye display section 30R are each disposed at positions shifted in the direction away from each other by a distance Ly from the respective positions illustrated in FIG. 7A. The distance between the left-eye display section 30L and the right-eye display section 30R is thereby widened from the distance Lw to a distance Lu (Lw<Lu).

Note that the convergence angle adjustment mechanism 31 may be any configuration capable of moving the left-eye display section 30L and the right-eye display section 30R in the inter-pupil direction of the observer OP (y axis direction), the convergence angle adjustment mechanism 31 may be a mechanism that is moved manually. Alternatively, the convergence angle adjustment mechanism 31 may be configured so as to be moved in response to a control signal from a control device (see FIG. 9) configured including a computer.

As illustrated in FIG. 7B, widening the distance between the optical units 42L, 42R from the distance Lw to the distance Lu results in the optical path from the center of the imaged image ImL and the optical path from the center of the imaged image ImR being oriented inwards so as to intersect at the exit side of the optical unit 42. However, these optical paths reach the two eyes of the observer OP by passing through the reflection member 48. Note that since the angles of the light rays in the y axis direction are inverted before emission from the reflection member 48, after emission the respective optical paths are now oriented outwards. This thereby enables a state to be achieved in which a convergence angle is caused to arise between the optical paths when the imaged images Im are viewed by the two eyes of the observer OP so as to intersect in front of the observer OP. Namely, a state can be achieved in which the imaged images ImL, ImR appear to be disposed at the inside of the optical axes CLL, CLR of the optical units 42L, 42R, so as to give rise to a convergence angle AC.

Figure 8:
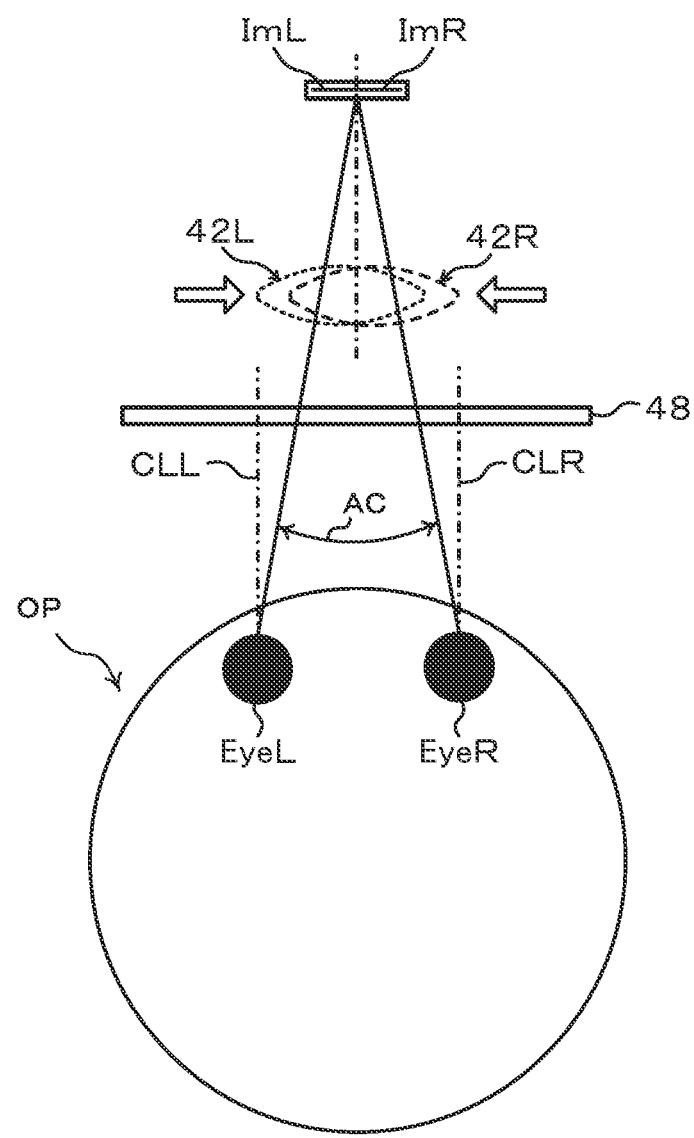
FIG. 8 is a schematic diagram illustrating an example of a viewing state of an observer according to an exemplary embodiment.

FIG. 8 schematically illustrates an example of a viewing state of the observer OP corresponding to the state in FIG. 7B. Note that the left-eye optical unit 42L and the right-eye optical unit 42R are illustrated in simplified form in FIG. 8. As illustrated in FIG. 8, a state in which the convergence angle AC can be caused to arise such that an intersection occurs in front of the observer OP, gives rise to a viewing state in which the respective optical units 42L, 42R appear to overlap with each other as viewed by the observer OP, such that there is consistency between the focal point of the observer OP and the convergence angle AC. This enables provision of the ophthalmic system 10 that satisfies both the first condition and the second condition.

By displaying the imaged images ImL, ImR having disparities for parallax in this manner, there is no reduction in the resolution of the image. Moreover, in the present exemplary embodiment, the convergence angle AC is unchanged since the observer OP focuses on a focal point at infinity and perceives an image at a distance for observing the display section 30 that can generally be seen clearly (for example 250 mm).

The convergence angle adjustment mechanism 31 described above may be driven based on a control signal from a control device configured including a computer.

Figure 9:
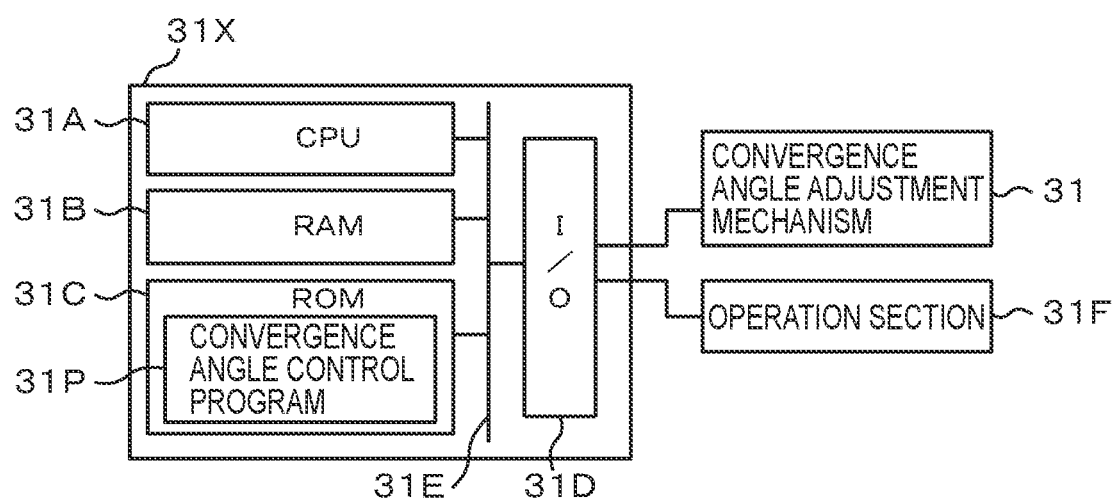
FIG. 9 is a block diagram illustrating an example of a control device for controlling driving of a convergence angle adjustment mechanism according to an exemplary embodiment in a configuration implemented by a computer.

FIG. 9 illustrates an example of configuration in which a control device that controls driving of the convergence angle adjustment mechanism 31 is implemented by a computer.

As illustrated in FIG. 9, the computer that operates as the control device is configured including a device main body 31X including a central processing unit (CPU) 31A, random access memory (RAM) 31B, and read only memory (ROM) 31C. The ROM 31C contains a convergence angle control program 31P for executing control to vary the convergence angle. The device main body 31X includes an input/output interface (I/O) 31D, and the CPU 31A, the RAM 31B, the ROM 31C, and the I/O 31D are connected so as to be capable of exchanging commands and data with each other through a bus 31E. The convergence angle adjustment mechanism 31 and an operation section 31F input with instructions and the like by the observer OP are connected to the I/O 31D.

The device main body 31X reads the convergence angle control program 31P from the ROM 31C and expands the convergence angle control program 31P in the RAM 31B. The device main body 31X operates as the control device performing control to vary the convergence angle the convergence angle control program 31P expanded in the RAM 31B being executed by the CPU 31A.

Figure 10:
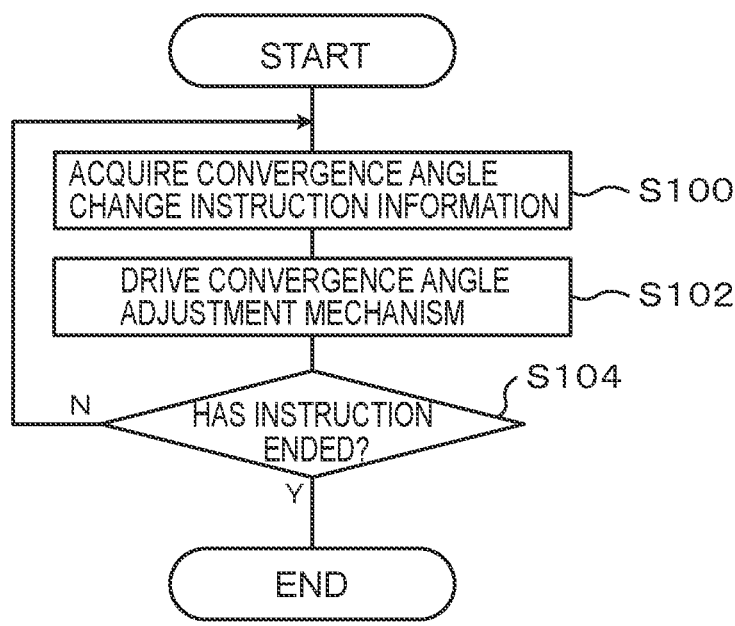
FIG. 10 is a flowchart illustrating an example of a flow of processing in a convergence angle control program according to an exemplary embodiment.

FIG. 10 illustrates an example of a flow of processing according to the convergence angle control program 31P in the control device that performs control to vary the convergence angle as implemented by the computer.

In the device main body 31X, the convergence angle control program 31P is read from the ROM 31C and expanded in the RAM 31B, and the convergence angle control program 31P expanded in the RAM 31B is executed by the CPU 31A.

Examples of an execution timing of the convergence angle control program 31P, namely a timing to vary the convergence angle, include when changing the magnification of the imaging section 20, when changing the type of surgery, and when changing the technician. An example of when the magnification of the imaging section 20 changes is when the optical magnification of the microscope 22 of the imaging section 20 has changed. An example of when the type of surgery changes is when the operating field changes, for example when changing from a procedure performed on an anterior eye portion of the examined eye to a procedure performed on a posterior eye portion of the examined eye, or a change in operating field in the opposite direction. An example of when the technician changes is when the practitioner responsible for carrying out a procedure changes.

First, at step S100, instruction information indicating a change of convergence angle is acquired. The instruction information is information representing an instruction given by operation of the operation section 31F by the observer OP. At the next step S102, a control signal to drive the convergence angle adjustment mechanism 31 is output based on the instruction information acquired at step S100. Namely, a control signal is output to indicate a distance between the left-eye display section 30L and the right-eye display section 30R as changed by the convergence angle adjustment mechanism 31. At the next step S104, determination is made as to whether or not the instruction given by operation of the operation section 31F by the observer OP has ended, and in cases in which determination is affirmative, the present processing routine is ended without further processing. On the other hand, in cases in which determination is negative at step S104, processing returns to step S100.

Either of the following two modes may be adopted during the processing from step S100 to step S104.

A first mode is a mode in which a control signal is output so as to move the distance between the left-eye display section 30L and the right-eye display section 30R by a predetermined prescribed amount at each time of instruction using the operation section 31F by the observer OP, such as each time the observer OP presses a button. For example, in this first mode each time an instruction is given using the operation section 31F to increase the convergence angle caused to arise between the two eyes of the observer OP, an incremental change is made from a current first distance to a second distance that is the prescribed amount greater than the first distance.

A second mode is a mode in which a control signal is output so as to continuously move the distance between the left-eye display section 30L and the right-eye display section 30R for as long as instruction by the observer OP continues using the operation section 31F, for example by holding down a button. The second mode enables the observer OP to change the convergence angle caused to arise between both eyes while viewing the image Im.

The reflection member 48 (optical image forming element 48A) has a property to focus light rays with plane-symmetry, and as a result of this property, light that passes through the reflection member 48 maintains its angle in the one direction but is inverted in angle in the other direction orthogonal to the one direction. There are therefore cases in which the image viewed by the observer OP is inverted such that the image is seen as being back-to-front from reality.

Figure 11:
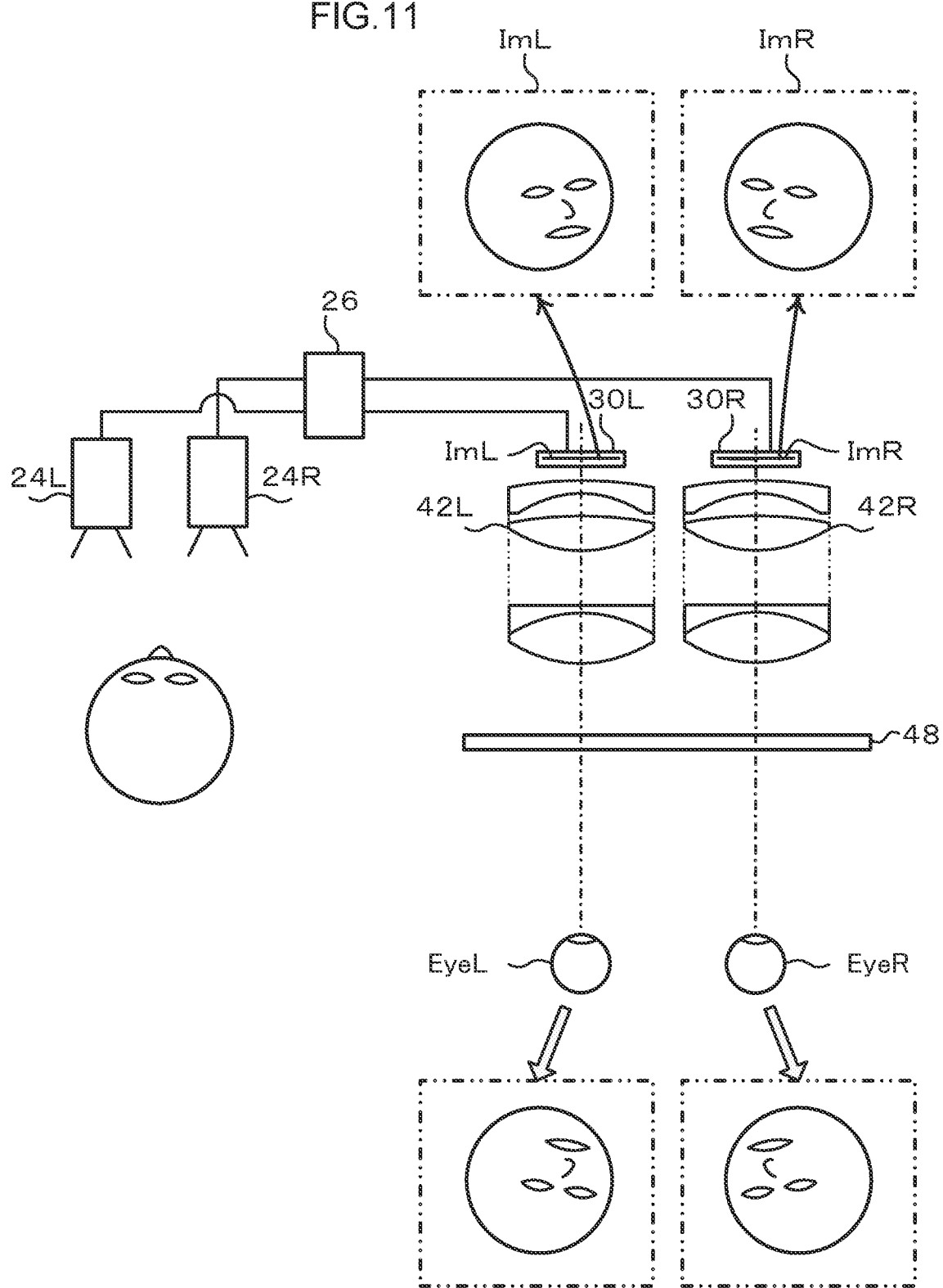
FIG. 11 is a schematic diagram illustrating an example of a relationship between imaged images according to an exemplary embodiment and images formed on the retinas of an observer.

FIG. 11 schematically illustrates an example of a relationship between the left-eye imaged image ImL and the right-eye imaged image ImR for the observer OP, and images formed on the retina of the observer OP when these images are viewed through the reflection member 48.

In the example illustrated in FIG. 11, the imaged image ImL displayed on the left-eye display section 30L is formed on the retina of the left eye EyeL of the observer OP so as to be inverted both vertically and horizontally. Similarly, the right-eye imaged image ImR is vertically and horizontally inverted on the retina of the right eye EyeR of the observer OP. The images are accordingly difficult to employ, for example, on a head mounted display (HMD) device as-is.

Accordingly, in the present exemplary embodiment, the imaged image Im displayed on the display section 30 is displayed so as to be perceived appropriately by the observer OP.

Figure 12:
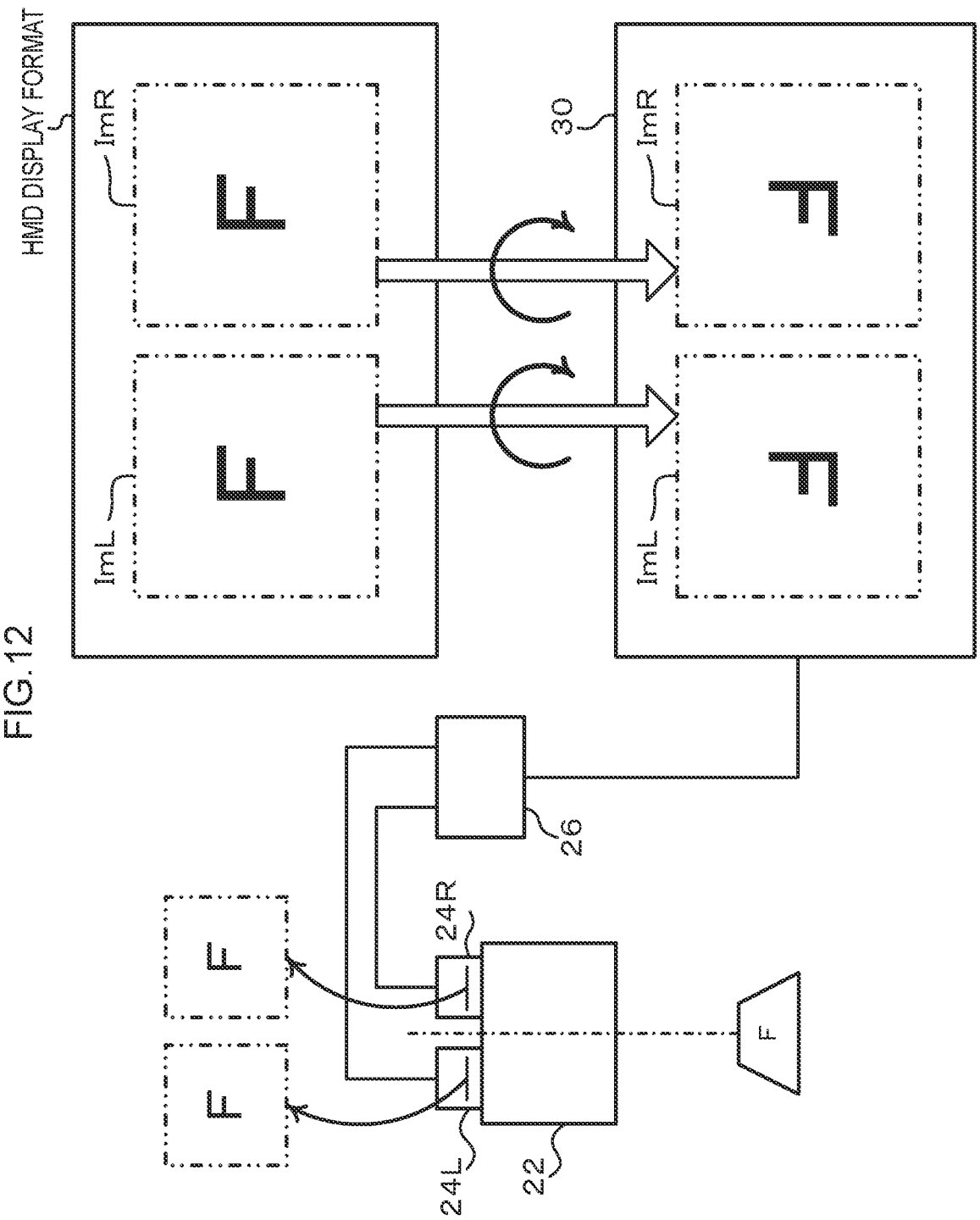
FIG. 12 is an illustration illustrating an example of imaged images displayed in a case in which an anterior eye portion of an examined eye is imaged using an ophthalmic system according to an exemplary embodiment.

FIG. 12 illustrates an example of the imaged image Im displayed on the display section 30 in a case in which the anterior eye portion of the examined eye is being imaged by the ophthalmic system 10 according to the present exemplary embodiment. Note that FIG. 12 illustrates a case in which both the imaged images ImL, ImR are being displayed on the display section 30.

As illustrated in FIG. 12, in the present exemplary embodiment each of the imaged images ImL, ImR displayed on the display section 30 are pre-inverted (namely rotated by) 180° with respect to a HMD display format. Note that processing to pre-invert (namely rotate by 180°) each of the imaged images ImL, ImR displayed on the display section 30 may be executed by the camera controller 26. In cases in which the respective imaged images ImL, ImR are to be associated and displayed on the respective display sections 30L, 30R, the display sections 30L, 30R may be rotated by 180° in advance.

In this manner, the respective imaged images ImL, ImR to be displayed on the display section 30 are pre-inverted (namely rotated by 180°) such that the imaged images ImL, ImR are displayed so as to perceived appropriately by the observer OP.

Moreover, when observing the examined eye, there are cases in which there is a demand to switch between observation of the anterior eye portion of the examined eye and observation of the posterior eye portion of the examined eye using the same microscope 22. For example, observation of the posterior eye portion may be realizable by inserting a front-end lens into the optical path of an observation light in a configuration of the microscope 22 for observing the anterior eye portion. Namely, it is possible to switch between anterior eye portion observation and posterior eye portion observation by inserting the front-end lens into the optical path of the observation light of the microscope 22, or removing the front-end lens therefrom. The front-end lens forms a primary image of the posterior eye portion (for example the ocular fundus) on the optical path of the microscope 22 in an optical system to re-form the primary image as a secondary image.

FIG. 13 illustrates an example of the imaged image Im displayed on the display section 30 in a case in which, so as to observe the posterior eye portion of the examined eye, a front-end lens 25 has been inserted at the examined eye side of the microscope 22 having the configuration for observing the anterior eye portion of the examined eye as illustrated in FIG. 12.

As illustrated in FIG. 13, when observing the posterior eye portion of the examined eye, the front-end lens 25 for forming a primary image is disposed on the examined eye side of the microscope 22 for observing the anterior eye portion of the examined eye as illustrated in FIG. 12, and the imaged images ImL, ImR are respectively imaged in an inverted state (namely rotated by 180°). The disparity due to parallax in the imaged images ImL, ImR is not inverted. In this manner, in cases in which the front-end lens 25 is disposed on the examined eye side of the microscope 22 to observe the posterior eye portion of the examined eye, the respective imaged images ImL, ImR displayed on the display section 30 are not subjected to being pre-inverted (namely rotated by 180°), and processing is executed by the camera controller 26 to swap over the imaged images ImL, ImR.

Due to swapping over the imaged images ImL, ImR displayed on the display section 30 in this manner, the respective imaged images ImL, ImR are displayed so as to be perceived appropriately by the observer OP.

Note that although explanation has been given regarding a case in which the front-end lens 25 that forms the primary image as described above is disposed to observe the posterior eye portion of the examined eye, in cases in which a front-end lens 25 disposed is not a lens that forms a primary image, a configuration similarly to when observing the anterior eye portion may be adopted, namely in which the respective imaged images ImL, ImR are pre-inverted (i.e. rotated by 180°).

The camera controller 26 may be implemented by a configuration including a computer.

Figure 14:
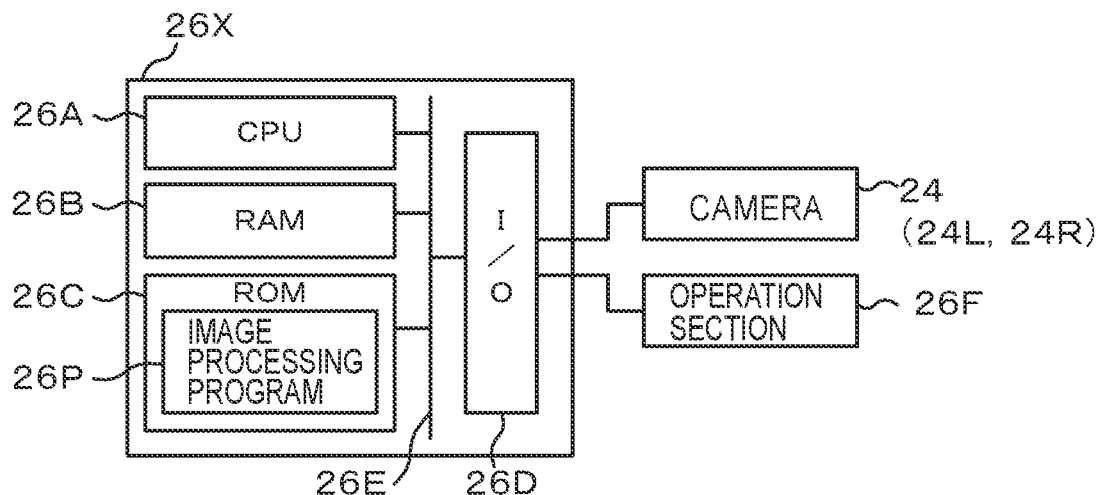
FIG. 14 is a block diagram illustrating an example of a configuration of a camera controller according to an exemplary embodiment.

FIG. 14 illustrates an example of a configuration in which the camera controller 26 is implemented by a computer.

As illustrated in FIG. 14, the computer that operates as the camera controller 26 is configured including a device main body 26X including a CPU 26A, RAM 26B, and ROM 26C. The ROM 26C contains an image processing program 26P for executing image processing such that the observer OP perceives the imaged image Im appropriately. The device main body 26X includes an input/output interface (I/O) 26D, and the CPU 26A, the RAM 26B, the ROM 26C, and the I/O 26D are connected to each other through a bus 26E so as to be capable of exchanging commands and data. The camera 24 and an operation section 26F input with instructions and the like by the observer OP are connected to the I/O 26D.

The device main body 26X reads the image processing program 26P from the ROM 26C, expands the image processing program 26P in the RAM 26B, and the image processing program 26P expanded in the RAM 26B is then executed by the CPU 26A. The device main body 26X accordingly operates as the camera controller 26 to perform image processing such that the observer OP is caused to perceive the imaged image Im appropriately.

Figure 15:
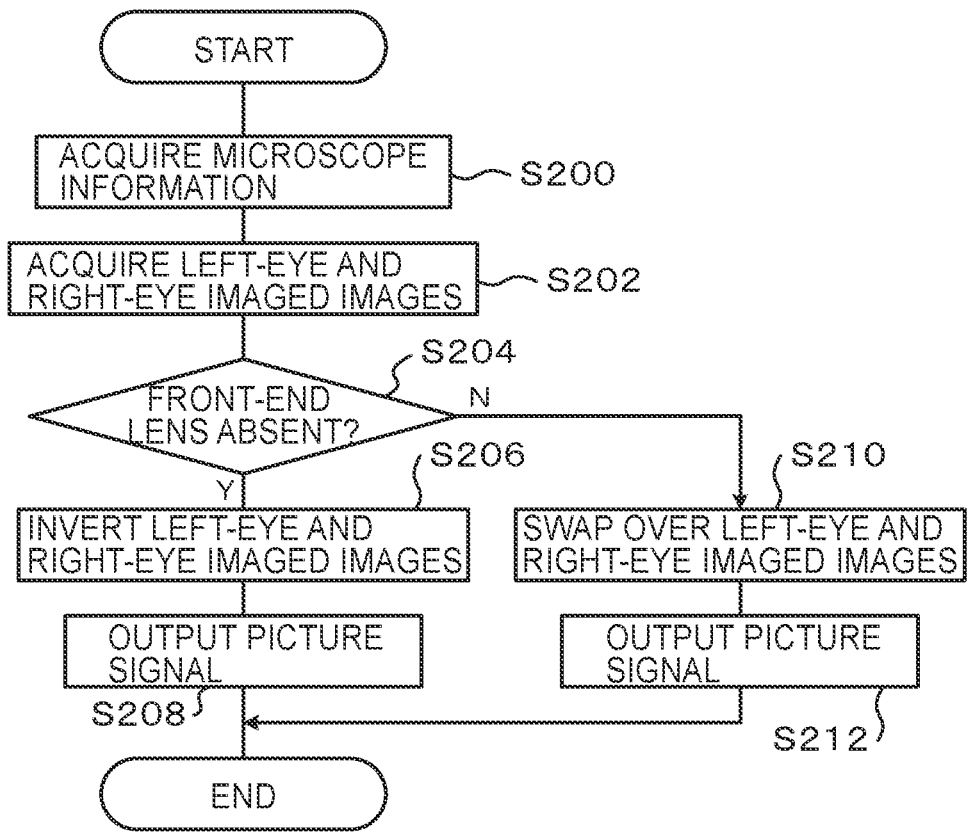
FIG. 15 is a flowchart illustrating an example of a flow of processing in an image processing program according to an exemplary embodiment.

FIG. 15 illustrates an example of a flow of processing according to the image processing program 26P in the camera controller 26 implemented by the computer.

In the device main body 26X, the image processing program 26P is read from the ROM 26C and expanded in the RAM 26B, and the image processing program 26P expanded in the RAM 26B is executed by the CPU 26A.

An example of an execution timing of the image processing program 26P is when the type of surgery changes, for example when the front-end lens 25 is inserted or removed.

First, at step S200, microscope information indicating the inserted/removed state of the front-end lens 25 is acquired. As the microscope information, information may be acquired representing an instruction from the observer OP using the operation section 26F, or a sensor may be provided to detect insertion or removal of the front-end lens 25 in the microscope 22, and the sensor output corresponding to insertion or removal of the front-end lens 25 may be acquired as the microscope information. At the next step S202, the respective imaged images ImL, ImR are acquired. At the next step S204, the inserted/removed state of the front-end lens 25 is determined based on the microscope information acquired at step S200. In cases in which the front-end lens 25 is in a removed state, determination at step S204 is affirmative as determination that the anterior eye portion is being observed, and processing transitions to step S206. At step S206, image processing is executed to invert (i.e. rotate by 180°) the respective imaged images ImL, ImR for display as images for anterior eye portion observation, and at the next step S208, a picture signal expressing the image-processed images is output to the display section 30.

In cases in which the front-end lens 25 is in a mounted state, then at step S204 determination is negative as determination that the posterior eye portion is being observed, and processing transitions to step S210. At step S210, so as to display the images for posterior eye portion observation, image processing is executed thereon to swap over imaged images ImL, ImR, without performing inversion processing on the respective imaged images ImL, ImR, and at the next step S212, a picture signal expressing the image-processed images is output to the display section 30.

In the foregoing explanation, the distance between the left-eye display section 30L and the right-eye display section 30R is widened in order to create a state that causes the convergence angle AC to arise between the two eyes of the observer OP (see FIG. 7B). However, technology disclosed herein is not limited to widening the distance between the left-eye display section 30L and the right-eye display section 30R in order to create a state that causes the convergence angle AC to arise. Namely, for the left eye, the relative relationship between the display section 30L and the optical unit 42L may be changed, and for the right eye, the relative relationship between the display section 30R and the optical unit 42R may be changed, so as to dispose the image centers at positions away from the optical axes of the respective optical units. The optical unit 42L and the optical unit 42R may accordingly be moved relative to the left-eye display section 30L and the right-eye display section 30R.

Figure 16:
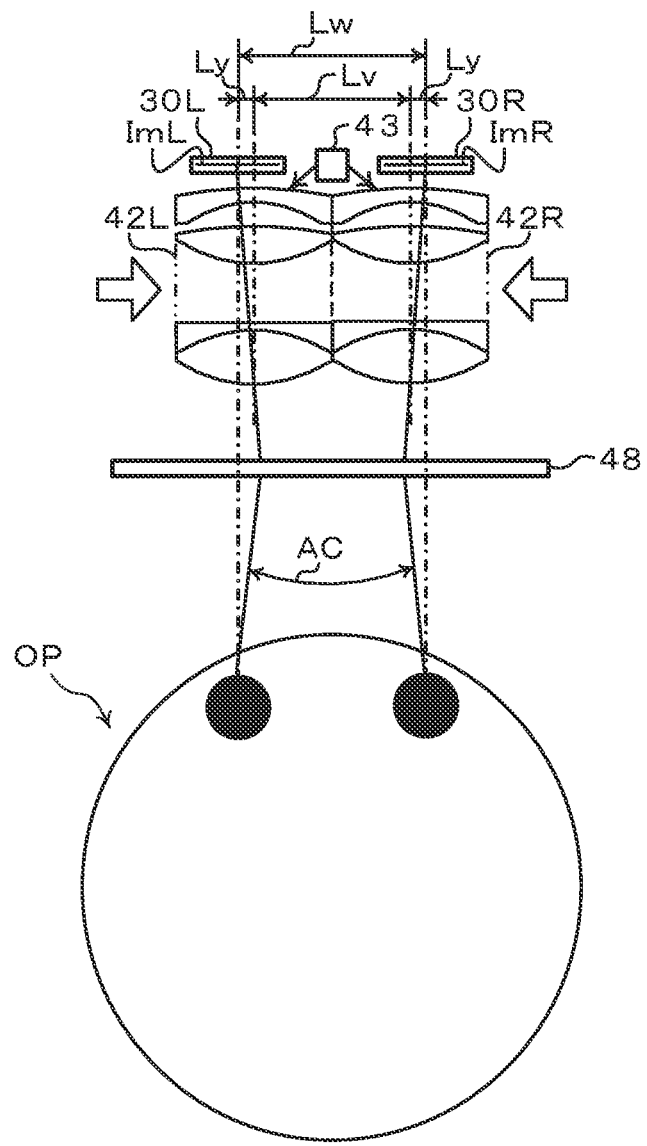
FIG. 16 is a schematic diagram illustrating a modified example of a display device according to an exemplary embodiment.

FIG. 16 schematically illustrates an example of optical paths of an image Im in a modified example of the display device 40 provided with the display section 30, in which the convergence angle AC is caused between the two eyes of the observer by moving the optical units 42L, 42R.

In the example illustrated in FIG. 16, the left-eye optical unit 42L and the right-eye optical unit 42R are formed so as to be capable of being moved in the y axis direction, this being the inter-pupil direction of the observer OP, by a convergence angle adjustment mechanism 43 for optical units. The left-eye optical unit 42L and the right-eye optical unit 42R are respectively disposed at positions moved toward each other by the distance Ly from positions at a pupil distance Lw. Accordingly, the distance between the optical axes of the left-eye optical unit 42L and the right-eye optical unit 42R is shortened from the distance Lw to a distance Lv (Lv<Lw). The ophthalmic system 10 formed as in the example illustrated in FIG. 16 is also capable of obtaining similar advantageous effects to those of the ophthalmic system 10 formed as in the example illustrated in FIG. 7B.

Note that when moving the optical units 42L, 42R, there is no limitation to moving the entirety of the optical units 42L, 42R, and a configuration may be adopted in which at least part of each of the optical units 42L, 42R is moved.

In the foregoing explanation, although explanation has been given regarding a case in which the display section 30 or the optical unit 42 is moved in the inter-pupil direction, configuration may be made so as to move both the display section 30 and the optical unit 42 relative to each other.

In the foregoing explanation, although explanation has been given regarding a case in which at least one out of the display section 30 and the optical unit 42 is moved in the inter-pupil direction, technology disclosed herein is for creating a state that causes the convergence angle AC to arise, and is not limited to movement in the inter-pupil direction. For example, a configuration may be adopted in which the respective optical axes of the left-eye optical unit 42L and the right-eye optical unit 42R are swung, namely, swung so as to intersect each other on the exit side of the optical unit 42.

Figure 17:
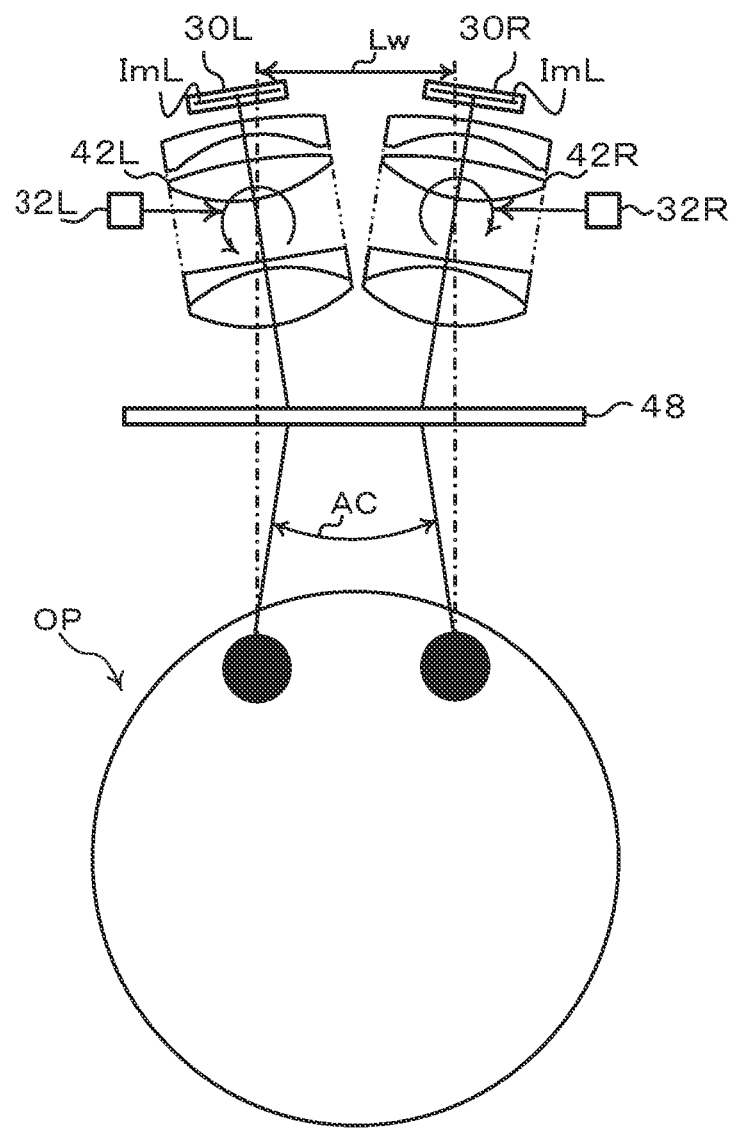
FIG. 17 is a schematic diagram illustrating another modified example of a display device according to an exemplary embodiment.

FIG. 17 schematically illustrates an example of optical paths of the images Im in another modified example of the display device 40 provided with the display sections 30, in which display sets of the display section 30 and the optical unit 42 are swung so as to cause a convergence angle AC between the two eyes of the observer OP.

In the example illustrated in FIG. 17, the optical axis of a left-eye display set configured by the left-eye display section 30L and the optical unit 42L is formed capable of being swung in a direction toward the inside on the exit side (the counterclockwise direction in FIG. 17) by a left-eye convergence angle adjustment mechanism 32L. Similarly, the optical axis of a right-eye display set configured by the right-eye display section 30R and the optical unit 42R is formed capable of being rotated in a direction toward the inside on the exit side (the clockwise direction in FIG. 17) by a right-eye convergence angle adjustment mechanism 32R. Rotating the display sets in this manner enables the convergence angle AC to be caused to arise.

Explanation follows regarding a positional relationship between the display section 30 and the optical unit 42.

When the observer OP views light, an image can be formed on the retina using parallel light, and due to the ability of the eyes to adjust, an image can also be formed on the retina using divergent light. However, even with the ability of the eyes to adjust it is still difficult to form an image on the retina using convergent light. For example, in cases in which the optical unit 42 has a curved image plane, placing an image at the focal point of the optical unit 42 causes parallel light to be emitted from the lens system in the vicinity of the optical axis, and an image to be formed on the retina by the eye of the observer OP viewing this parallel light. However, at positions away from the optical axis, the action of the curved image plane causes convergent light to be emitted from the optical unit 42, and the image not to be formed on the retina even when the observer OP views this convergent light.

In the ophthalmic system 10 according to the present exemplary embodiment, due to emitted light from the optical unit 42 reaching the observer OP through the reflection member 48, an image can be formed on the retina by the observer OP adjusting their eyes.

FIG. 18 schematically illustrates a positional relationship between the display section 30 and the optical unit 42.

As described above, although the reflection member 48 (optical image forming element 48A) is an element that lets light pass through, due to the structure of the reflection member 48, for light rays passing through the reflection member 48 an angle is maintained in one direction and is inverted in angle in another direction orthogonal to the one direction. Namely, as illustrated in FIG. 18, in cases in which light is incident to the reflection member 48 is convergent due to due to the action of the curved image plane, the light emitted therefrom is converted into divergent light. This enables the observer OP to view the image by adjusting their eyes. Using the reflection member 48 to invert the convergent light to become divergent light enables the observer OP to view the image even when the optical unit 42 has a curved image plane. This enables a reduction to be achieved in the processing effort put in during optical design to suppress a curved image plane from arising in the optical unit 42. Moreover, the display device 40 of the ophthalmic system 10 can be formed merely by performing the straightforward task of setting the center of the image Im displayed on the display section 30 at the focal point position of the optical unit 42.

Next, explanation follows regarding driving of the reflection member 48 to assist image viewing by the observer OP.

As described above, the reflection member 48 includes plural elements for reflecting light and letting light pass through. Due to this structure of the reflection member 48, cases may arise in which, for example, the observer OP views light scattered at a reflection surface, and the observer OP aligns the focal point of their viewing to an element or a part of the element of the reflection member 48, resulting in the element or part of the element of the reflection member 48 hindering image viewing.

The ophthalmic system 10 according to the present exemplary embodiment is therefore provided with a suppression mechanism to suppress the observer OP from aligning the focal point of their viewing on the reflection member 48. In the present exemplary embodiment, as an example of a suppression mechanism, the reflection member 48 is moved in a prescribed direction to suppress viewing by the observer OP alighting on the reflection member 48. Note that reference to light "passing through" the reflection member 48 designed to let light pass through, refers to a light progression state by at least one action out of light being reflected at a reflection surface, light being transmitted, light transitioning mediums, and light progression with a deflected optical path due to refraction.

Figure 19A:
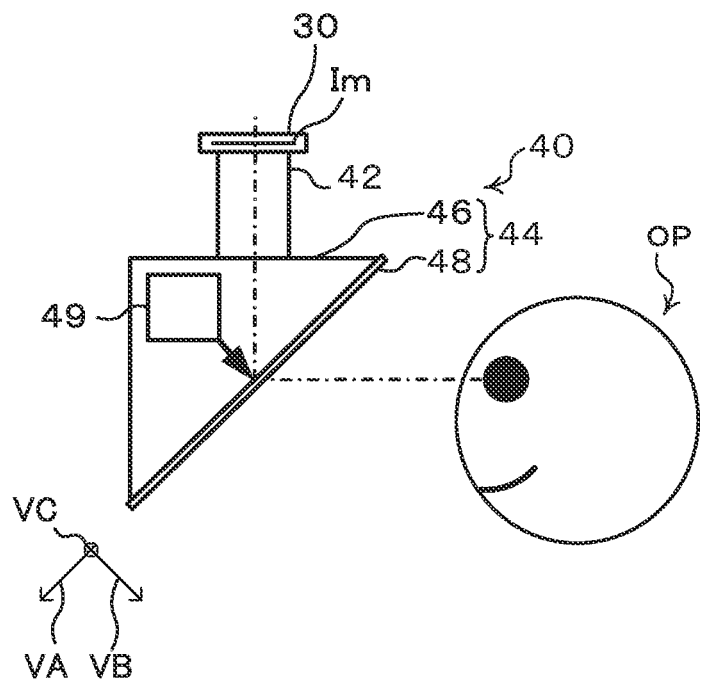
FIG. 19A is an illustration illustrating an example of configuration of a suppression mechanism in an ophthalmic system according to an exemplary embodiment.
Figure 19B:
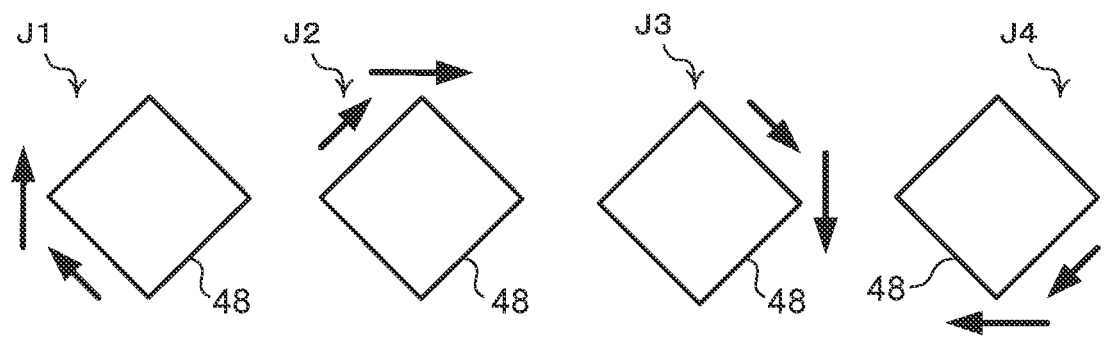
FIG. 19B is an illustration illustrating an example of driving a reflection member in an ophthalmic system according to an exemplary embodiment.

FIG. 19A and FIG. 19B schematically illustrate an example of a suppression mechanism 49. FIG. 19A illustrates an example of a configuration of the suppression mechanism 49. FIG. 19B illustrates an example of driving of the reflection member 48. The suppression mechanism 49 drives the reflection member 48 either periodically or non-periodically such that the reflection member 48 is not stationary at the same position.

As illustrated in FIG. 19A, the suppression mechanism 49 is a drive section for driving so as to move the reflection member 48 in at least one direction from out of a direction (arrow VB direction) normal to the surface of the reflection member 48, different directions (arrow VA and VC directions) intersecting with the normal direction, or directions of rotation thereabout. The suppression mechanism 49 preferably drives the reflection member 48 so as to maintain the exit angle from the reflection member 48. Namely, the suppression mechanism 49 performs at least one type of driving out of movement in at least one direction orthogonal to the reflection member 48 or rotation offset from a central position, while the reflection member 48 maintains the exit angle of the reflected light. The reflection member 48 is preferably driven periodically in consideration of the inspection periodicity when the observer OP is pinpointing an object. For example, the drive periodicity is preferably set to a periodicity of at least 30 Hz. In cases in which the reflection member 48 is configured by stacked reflection surfaces at a prescribed pitch (for example 0.2 mm), driving is preferably performed such that the movement amount is no greater than the prescribed pitch (for example 0.2 mm).

FIG. 19B illustrates an example of driving of the reflection member 48 that enables emission from the reflection member 48 while maintaining a parallel state of the emitted light. The example of FIG. 19B illustrates a drive sequence for driving the reflection member 48 for a configuration of the reflection member 48 having an eccentricity amount corresponding to the pitch width of the prescribed pitch. A first state J1 is a state for driving the reflection member 48 so as to move the reflection member 48 such that a reflection surface maintains a displacement according to movement in a prescribed pitch width direction, and a second state J2 is a state for driving the reflection member 48 so as to move the reflection member 48 such that a reflection surface maintains a displacement according to movement in the prescribed pitch width direction for the next reflection surface. After driving in a similar manner with a state of a third state J3 and a fourth state J4, driving then returns to the first state J1. The focal point of viewing by the observer OP is suppressed from alighting on the reflection member 48 due to agitating the reflection member 48 through the first state J1 to the fourth state J4.

Driving the reflection member 48 with the suppression mechanism 49 suppresses the focal point of the view of the observer OP from alighting on the reflection member 48.

Note that the suppression mechanism 49 is an example of a device to perform at least one type of driving out of vibration or rotation, and examples thereof include drive devices that perform at least one type of driving out of linear driving, curved driving, or rotational driving.

In the foregoing explanation, explanation has been given regarding an example in which the reflection member 48 is driven to suppress the reflection member 48 from being seen by the observer OP. Next, explanation follows regarding an example in which a visible object 47 is disposed in the direction of viewing of the observer OP and before reaching the reflection member 48 so as to actively suppress viewing of the reflection member 48.

Light emitted from the optical unit 42 reaches the eyes of the observer OP after passing through the reflection member 48 and forms an image on the retina of the observer OP such that the observer OP perceives the imaged image Im. The visible object 47, configured by a frame or the like, is disposed at a position that is viewable by the observer OP and is a position not blocking the light emitted from the optical unit 42.

Figure 20:
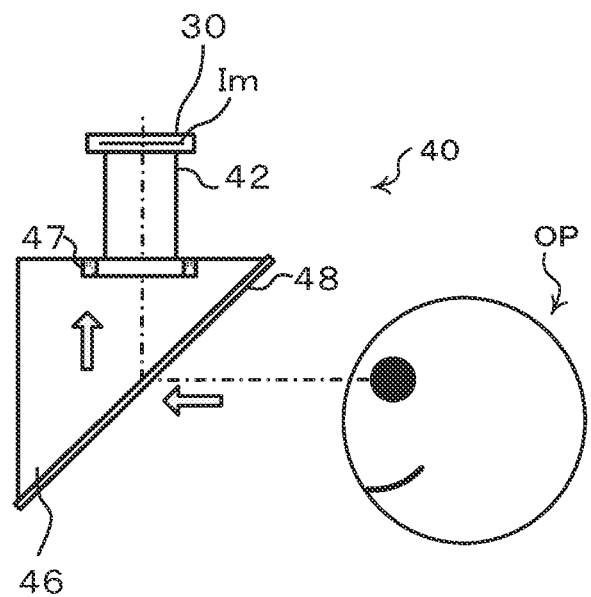
FIG. 20 is an illustration illustrating an example of a display device according to an exemplary embodiment having a visible object disposed therein.

FIG. 20 illustrates an example of display device 40 with the visible object 47 disposed therein. FIG. 20 illustrates an example of configuration in a case in which the reflection member 48 is a reflection-type reflection member, and in which the light emitted from the optical unit 42 is reflected by the reflection member 48 before reaching the eyes of the observer OP. In the example illustrated in FIG. 20, the gaze of the observer OP is directed toward the optical unit 42 (also indicated by arrows in FIG. 20). Accordingly, the observer OP is able to view the light exit side of the optical unit 42. The visible object 47 such as a frame is disposed at a position which is peripheral to the optical unit 42 and is a position not blocking the light emitted from the optical unit 42, for example, by disposing at an outer edge portion of the optical unit 42. The observer OP views the visible object 47 as a reflection from the reflection member 48, thereby suppressing the observer OP from viewing the reflection member 48. The visible object 47 accordingly functions as a fixation target for the observer OP. Note that the visible object 47 may be a physical object capable of being viewed by the observer OP, or may be an image or a point of light from a light source.

Figure 21:
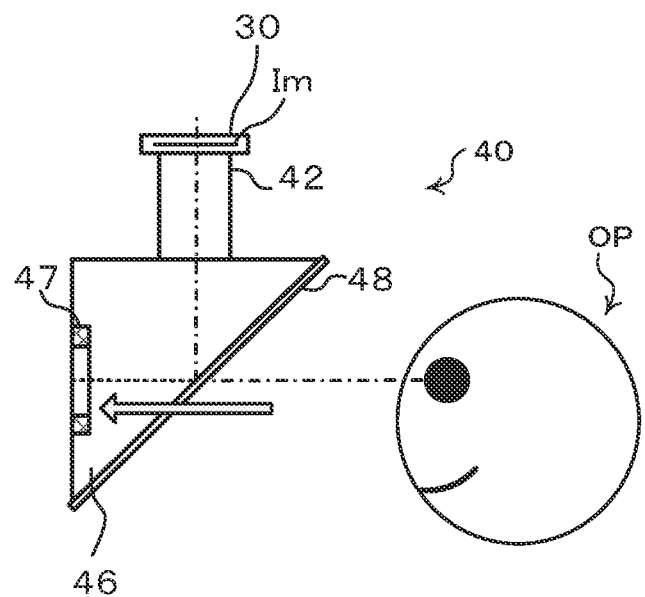
FIG. 21 is an illustration illustrating an example of a display device according to an exemplary embodiment having a visible object disposed therein.

FIG. 21 illustrates another example of a display device 40 disposed with the visible object 47. FIG. 21 illustrates an example of configuration in a case in which the reflection member 48 with transparent properties. In cases in which the reflection member 48 has transparent properties, the gaze of the observer OP passes through the reflection member 48 and continues straight on (illustrated by arrows in FIG. 20). The visible object 47 such as a frame is disposed in the gaze direction of the observer OP at a position that does not block the light emitted from the optical unit 42, for example at a prescribed position inside the case 46. The observer OP views the visible object 47 through the transmission-type of reflection member 48, thereby suppressing the observer OP from viewing the reflection member 48.

Note that cases may arise in which the viewing contrast of the imaged image Im decreases due to light scattering when ambient light (for example light that escapes from the device, interior lighting, natural light, and so on) penetrates into the interior of the case 46 of the display device 40. It is therefore preferable to eliminate any light that could cause a decrease in contrast of the imaged image Im inside the display device 40, and in particular inside the case 46. The display device 40 according to the present exemplary embodiment may therefore be provided with an ambient light suppression section 50 to suppress light scattering of ambient light or the like inside the case 46.

Figure 22:
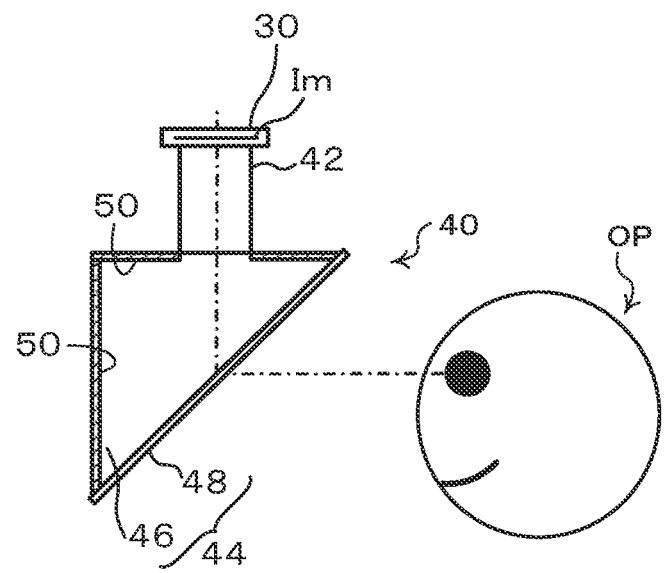
FIG. 22 is an illustration illustrating an example of an ambient light suppression section according to an exemplary embodiment.

FIG. 22 illustrates an example of the ambient light suppression section 50 disposed in the display device 40.

As illustrated in FIG. 22, the ambient light suppression section 50 is disposed within the case 46 of the display device 40 at a position that does not block the light emitted from the optical unit 42. For example, the ambient light suppression section 50 is disposed at an inner face of the case 46 on an extension line of the gaze of the observer OP through the reflection member 48 and an inner face of the case 46 on an extension line of the gaze of the observer OP as reflected by the reflection member 48. Note that an opening to let light emitted from the optical unit 42 pass through is provided in the ambient light suppression section 50 disposed at the inner face of the case 46 on the extension line of the gaze of the observer OP as reflected by the reflection member 48. The ambient light suppression section 50 is preferably capable of suppressing at least scattered light within the case 46 arising due to ambient light, and is more preferably capable of blocking such light. The ambient light suppression section 50 therefore preferably includes a light absorbing member. By including a light absorbing member, the ambient light suppression section 50 not only suppresses scattered light within the case 46 arising due to ambient light, but also suppresses reflection of light at the ambient light suppression section 50.

Note that the view angle of the light of the imaged images Im emitted from the optical unit 42 toward the reflection member 48 is an angle of view range (field of view angle) of the field of view of the observer OP in which the imaged image Im is viewable. Accordingly, taking the exit pupil as a reference, a region outside the field of view angle range of the observer OP in which the imaged image Im is viewable does not affect viewing (perceiving) of the imaged image Im by the observer OP. Providing a light blocking member in a region lying outside the field of view angle range of the observer OP, for example externally to the case 46, enables ambient light to be further suppressed.

Figure 23A:
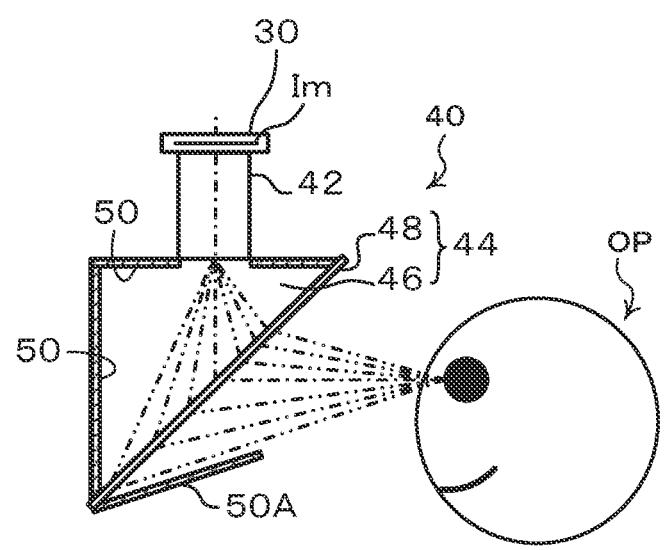
FIG. 23A is an illustration illustrating another example of an ambient light suppression section according to an exemplary embodiment.
Figure 23B:
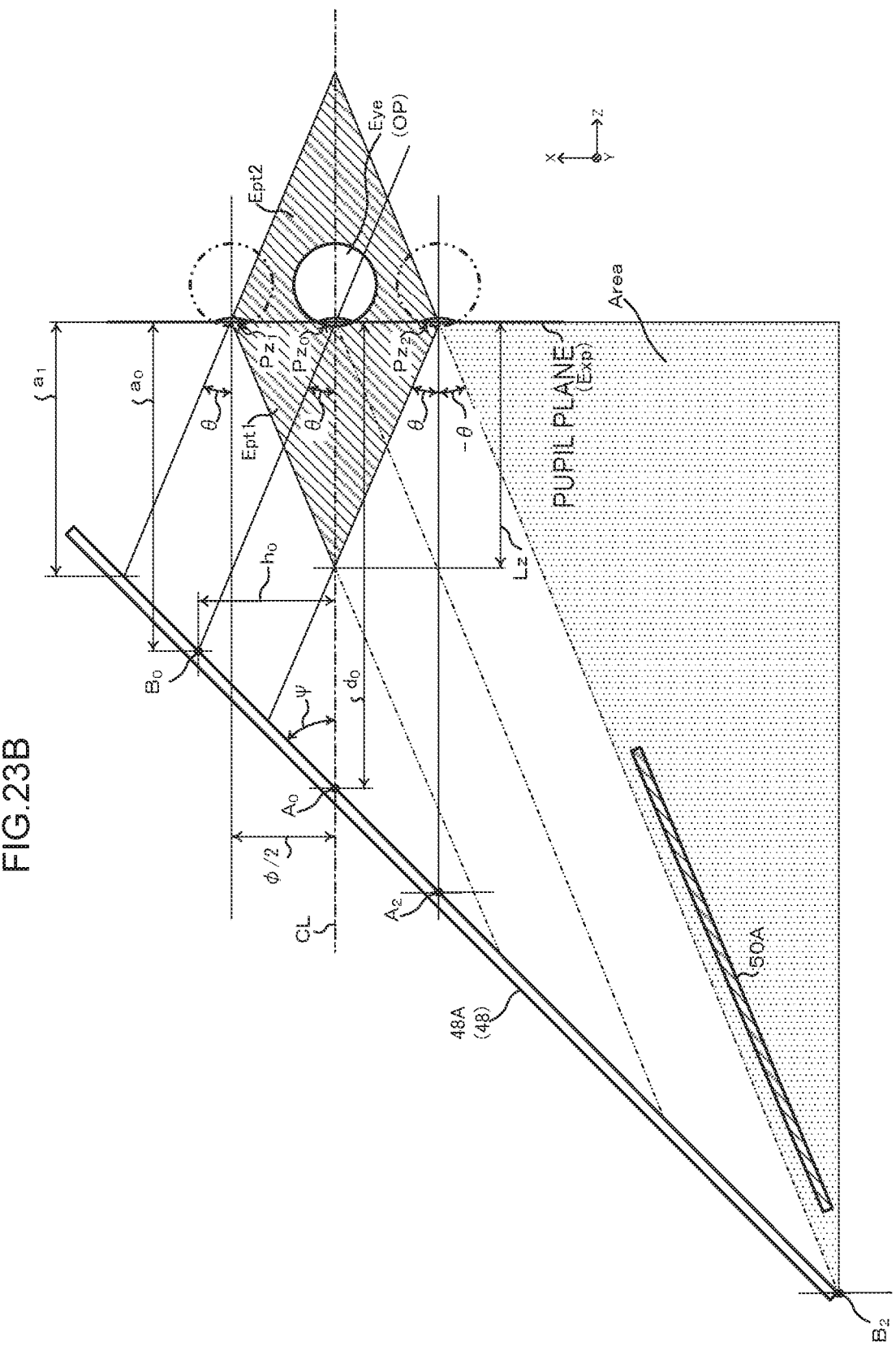
FIG. 23B is an illustration illustrating another example of an ambient light suppression section according to an exemplary embodiment.

FIG. 23A and FIG. 23B illustrate another example of an ambient light suppression section to further suppress ambient light. For example, ambient light incident to the reflection member 48 of the display device 40 may be detrimental to the imaged image Im visibility for the observer OP due to being reflected by the surface of the reflection member 48 such that the reflected light enters the field of view of the observer OP.

Accordingly, in the example illustrated in FIG. 23A and FIG. 23B, in addition to the ambient light suppression section 50 illustrated in FIG. 22, a plate shaped light blocking member 50A is provided to the case 46 of the display device 40 and disposed below the case 46 (in the −x axis direction). The light blocking member 50A is disposed so as not to block the field of view of the observer OP for perceiving the imaged image Im, and is parallel to the light rays passing through the angle range (field of view angle) of the maximum field of view of the observer OP for perceiving the imaged image Im. The distance from one end of the light blocking member 50A on the side of the display device 40 and the other end of the light blocking member 50A on the side of the observer OP is appropriately set such that the observer OP does not contact the light blocking member 50A within a variable range for the viewing position of the observer OP.

Note that although FIG. 23A illustrates an example in which the plate shaped light blocking member 50A is disposed below the case 46, the placement position and shape of the light blocking member 50A are not limited to those in the example illustrated in FIG. 23A. For example, the light blocking member 50A may be positioned at any position that does not block the field of view of the observer OP for perceiving the imaged image Im, and may have any shape (for example a polygonal shape such as a square or rectangular shape, a circular shape, a plate shape, or the like). Although FIG. 23A illustrates an example in which a single light blocking member 50A is disposed below the case 46, two or more of the light blocking member 50A may be thus disposed.

FIG. 23B illustrates an example of a placement position of the light blocking member 50A. In FIG. 23B, a position $Pz_2$ is set at a lower edge of the pupil at a position symmetrical about the optical axis CL to the pupil upper end $Pz_1$ described above, and $B_2$ is an intersection point between the reflection member 48 and a lower side (−x axis direction) half-angle (−θ in FIG. 23B) of the field of view at the pupil lower edge position $Pz_2$. The light blocking member 50A is disposed at the lower side (−x axis direction side) of the pupil lower edge position $Pz_2$ as referenced against a line (reference line) joining the intersection point $B_2$ and the pupil lower edge position $Pz_2$, where the pupil is positioned when the pupil is set at the pupil lower edge position $Pz_2$ (or a plane including such a line (reference plane)). In particular, the light blocking member 50A is effective if disposed within a region Area demarcated by the pupil plane, a reference (reference line, reference plane) joining the position $Pz_2$ and the intersection point $B_2$, and a horizontal line passing through the intersection point $B_2$ (in the Z axial direction). The light blocking member 50A is therefore disposed at a position along the reference or below the reference (for example below (in the −x axis direction) the position $Pz_2$, the case 46, or the reflection member 48) that does not block the eye box, while reducing surface reflection of ambient light at the reflection member 48 of the display device 40.

Although in the present exemplary embodiment an example of the ophthalmic system 10 has been described in which as an example of the reflection member 48, the optical image forming element 48A that can be treated as a recursive pass-through element is employed, the reflection member 48 is not limited to the optical image forming element 48A. For example, a reflective-type recursive element that includes functionality that does not change the progression direction of a light bundle when replicating in space may also be employed therefor. Explanation follows regarding an example thereof.

Figure 24A:
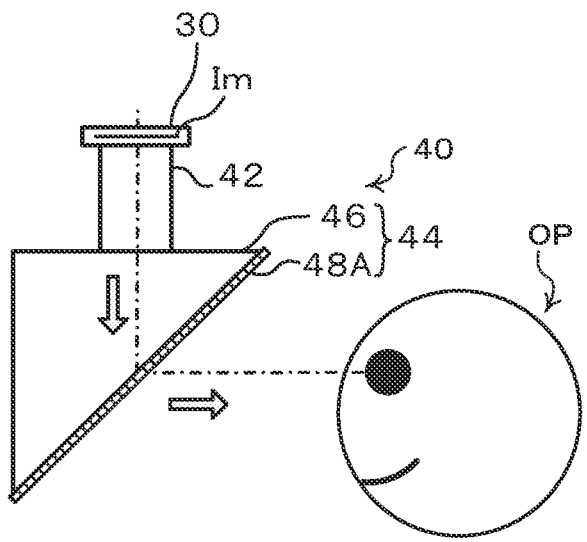
FIG. 24A is a schematic diagram illustrating an example of an employed image forming element relating to a reflection section of a display device according to an exemplary embodiment.
Figure 24B:
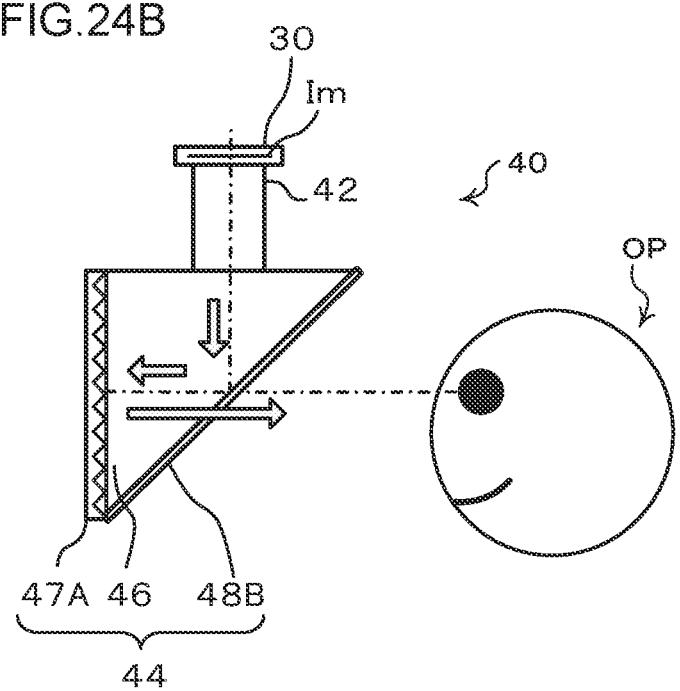
FIG. 24B is a schematic diagram illustrating a first modified example relating to a reflection section of a display device according to an exemplary embodiment.

FIG. 24A and FIG. 24B schematically illustrate an example of the display device 40 of the ophthalmic system 10.

FIG. 24A illustrates an example of the display device 40 of the ophthalmic system 10 employing an optical image forming element 48A that can be treated as a recursive pass-through element according to the present exemplary embodiment. FIG. 24B illustrates a first modified example related to the display device 40 of the ophthalmic system 10 employing a reflection-type recursive element.

As illustrated in FIG. 24A, in the display device 40 employing the optical image forming element 48A, the light emitted from the optical unit 42 is reflected by the reflection member 48 before reaching the eyes of the observer OP.

On the other hand, as illustrated in FIG. 24B, the reflection section 44 included in the display device 40 of the first modified example includes a case 46, a recursive reflection member 47A such as a reflection array in which plural corner cubes equipped with plural orthogonal reflection surfaces are arrayed in a two-dimensional flat plane shape, and a half mirror 48B. The display device 40 of the first modified example reflects light emitted from the optical unit 42 using the half mirror 48B. The light reflected by the half mirror 48B is emitted toward the recursive reflection member 47A, is recursively reflected thereat, passes through the half mirror 48B, and is emitted toward the observer OP. Since the first modified example illustrated in FIG. 24B employs light reflected by the half mirror 48B in this manner, the recursive reflection member 47A can be made smaller in size than the optical image forming element 48A of the display device 40 illustrated in FIG. 24A.

Second Modified Example

Figure 25:
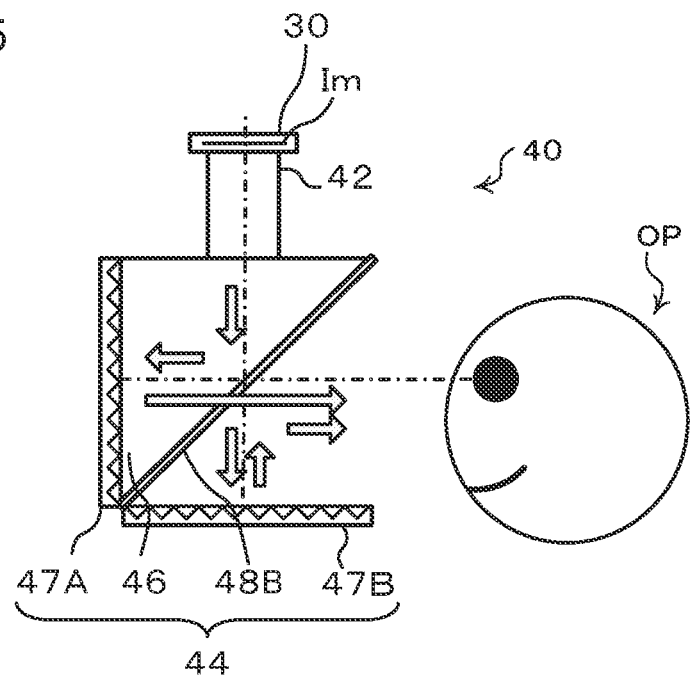
FIG. 25 is a schematic diagram illustrating a second modified example relating to a reflection section of a display device according to an exemplary embodiment.

FIG. 25 illustrates a second modified example related to the display device 40 of the ophthalmic system 10.

As illustrated in FIG. 25, in the second modified example, a reflection section 44 included in the display device 40 includes a case 46, recursive reflection members 47A, 47B such as reflection arrays in which plural corner cubes equipped with plural orthogonal reflection surfaces are arrayed in a two-dimensional flat plane shape, and a half mirror 48B. In the display device 40 of the second modified example, light emitted from the optical unit 42 is reflected by the half mirror 48B. The light reflected by the half mirror 48B is emitted toward the recursive reflection member 47A, is recursively reflected thereat, passes through the half mirror 48B, and is emitted toward the observer OP. Moreover, light that has passed through the half mirror 48B from out of the light emitted from the optical unit 42 is emitted toward the recursive reflection member 47B, is recursively reflected thereat, is reflected by the half mirror 48B, and is emitted toward the observer OP.

The second modified example is able to utilize the light that has passed through the half mirror 48B, and this thereby enables the light intensity of the imaged image Im viewed by the observer OP to be increased in comparison to in the first modified example.

Figure 26:
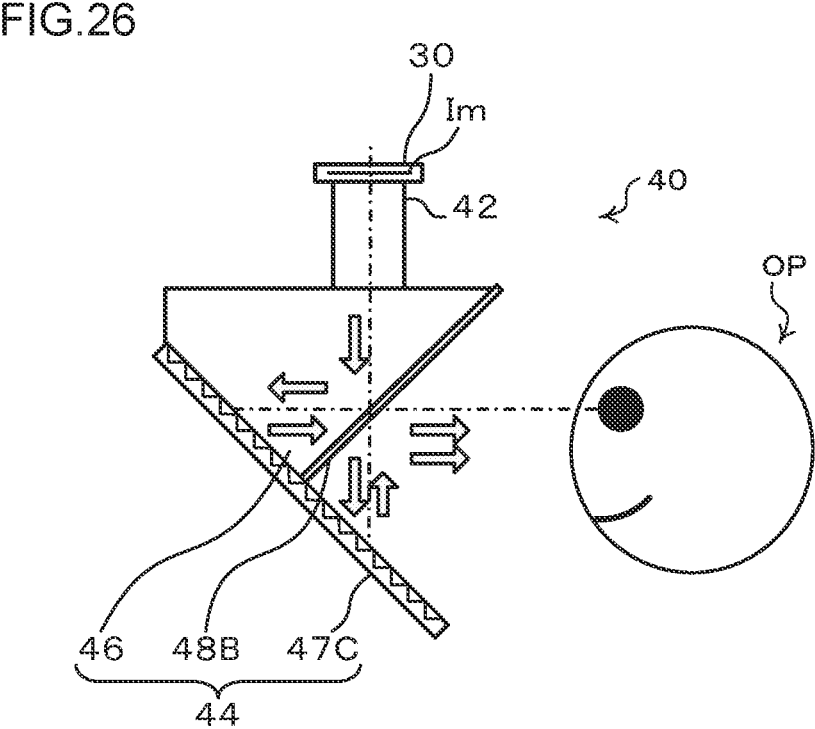
FIG. 26 is a schematic diagram illustrating a third modified example relating to a reflection section of a display device according to an exemplary embodiment.

FIG. 26 illustrates a third modified example related to the display device 40 of the ophthalmic system 10.

As illustrated in FIG. 26, in the third modified example the reflection section 44 included in the display device 40 includes a case 46, a recursive reflection member 47C such as a reflection array in which plural corner cubes equipped with plural orthogonal reflection surfaces are arrayed in a two-dimensional flat plane shape, and a half mirror 48B. Regarding the recursive reflection member 47C and the half mirror 48B, one end side of the half mirror 48B is disposed in the vicinity of the center of the recursive reflection member 47C such that the reflection surface or half mirror 48B and the reflection surface of the recursive reflection member 47C are orthogonal to each other. In the display device 40 of the third modified example, the light emitted from the optical unit 42 is reflected by the half mirror 48B. The light reflected by the half mirror 48B is emitted toward the recursive reflection member 47C, is recursively reflected thereat, passes through the half mirror 48B, and is emitted toward the observer OP. Moreover, the light that has passed through the half mirror 48B from out of the light emitted from the optical unit 42 is emitted toward the recursive reflection member 47C, is recursively reflected thereat, is reflected by the half mirror 48B, and is emitted toward the observer OP.

Thus in the third modified example, due to the reflected light and the light that has passed through the half mirror 48B both being recursively reflected by the common recursive reflection member 47C, a display device can be formed in which the number of elements of recursive reflection member is reduced in comparison to the second modified example.

Note that the reflection member of the reflection section 44 may employ a prism sheet mirror in which dihedral corner reflectors are arrayed in one direction.

Although the first modified example to the third modified example above have been described in relation to the display device 40 of the ophthalmic system 10, obviously similar advantageous effects are exhibited by each of the first modified example to the third modified example in cases in which the optical image forming element 48A is employed as the reflection member 48.

Note that although in the present exemplary embodiment a case has been described in which the optical image forming element 48A that forms an image at the same magnification is employed as an example of the reflection member 48, the reflection member 48 is not limited to the optical image forming element 48A that forms an image at the same magnification. The reflection member 48 may employ an element that forms an image not at the same magnification.

Figure 27A:
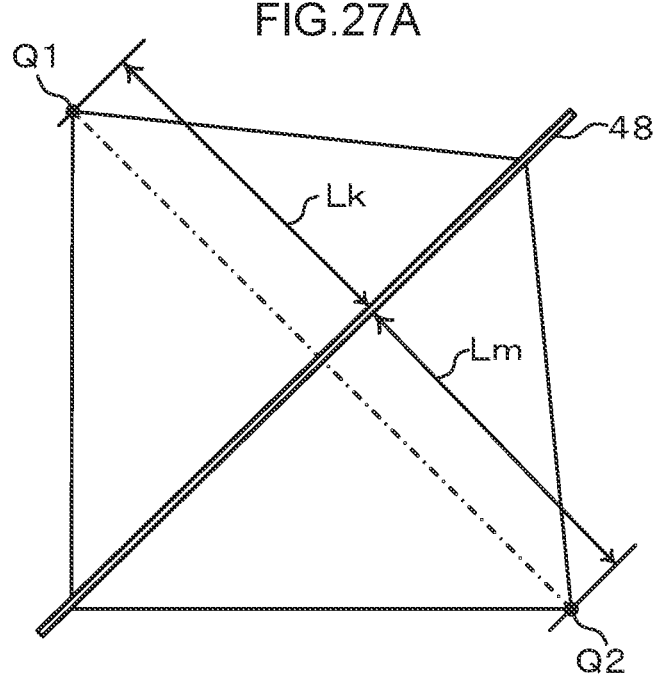
FIG. 27A is a schematic diagram relating to image forming by a reflection member according to an exemplary embodiment, illustrating an example of optical paths in a reflection member that forms an image at the same magnification.
Figure 27B:
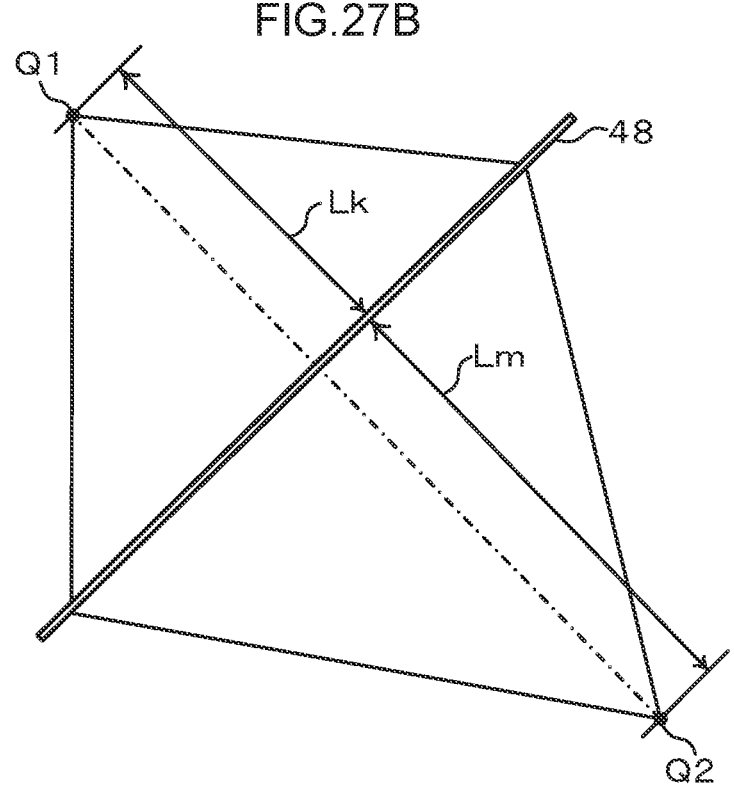
FIG. 27B is a schematic diagram relating to image forming by a reflection member according to an exemplary embodiment, illustrating an example of optical paths in a reflection member that forms an image not at the same magnification.

FIG. 27A and FIG. 27B schematically illustrate optical paths relating to image formation by the reflection member 48. FIG. 27A illustrates a reflection member 48 that forms an image at the same magnification, and FIG. 27B illustrates a reflection member 48 that forms an image not at the same magnification.

The reflection member 48 illustrated in FIG. 27A has a property of focusing light rays with plane symmetry, and a distance Lk from an object point Q1 to the reflection member 48 matches a distance Lm from an image point Q2 to the reflection member 48 (Lk=Lm). Accordingly, the reflection member 48 is, for example, capable of re-forming a pupil at the same size (same magnification of 1:1).

The reflection member 48 illustrated in FIG. 27B also has a property of focusing light rays with plane symmetry, but the distance Lk from the object point Q1 to the reflection member 48 does not match the distance Lm from the image point Q2 to the reflection member 48 (in the example of FIG. 27B, Lk<Lm). Accordingly, the reflection member 48 is, for example, capable of re-forming a pupil at the same size (magnification of 1:m). Note that since elements that form images not at the same magnification and are applicable as the reflection member 48 are known technology, such as described in JP-A No. 2017-067933, detailed explanation thereof is omitted.

The reflection member 48 according to the present exemplary embodiment is capable of providing additional refractive power. For example, the reflection member 48 may be understood to encompass a reflection element known as a lobster eye capable of providing additional refractive power by bending the reflection member 48 so as to impart curvature.

Figure 28:
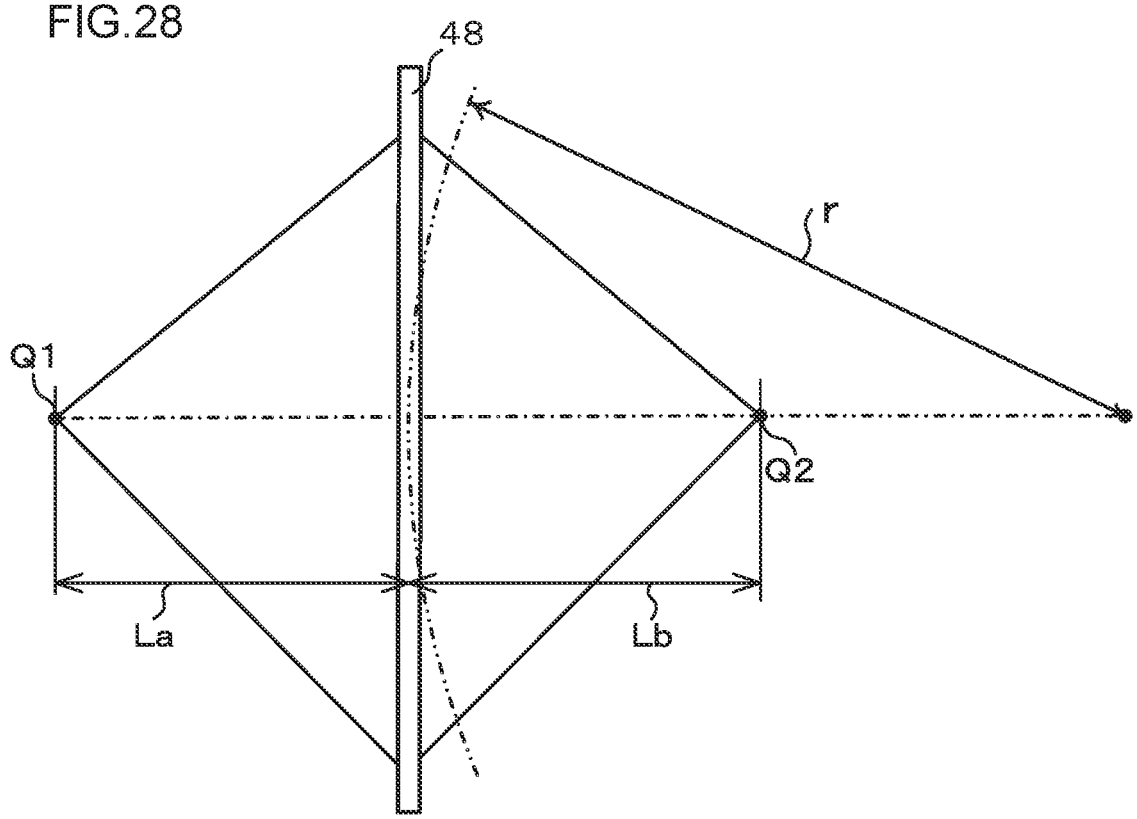
FIG. 28 is a schematic diagram illustrating a reflection member capable of providing additional refractive power according to an exemplary embodiment.

FIG. 28 schematically illustrates a reflection member 48 capable of providing additional refractive power.

FIG. 28 illustrates an example of the reflection member 48 employing an optical image forming element 48A that forms an image at the same magnification. Namely, the flat plane shaped reflection member 48 as illustrated in FIG. 28 has a property of focusing light rays with plane symmetry, and a distance La from an object point to the reflection member 48 matches a distance Lb from an image point Q2 to the reflection member 48 (La=Lb). As illustrated in FIG. 28, the flat plane shaped reflection member 48 is capable of imparting a refractive power of 2/r by being formed so as to have a curvature of radius r.

Next, explanation follows regarding a magnification β of the reflection member 48 imparted with the refractive power of 2/r.

For ease of explanation, the focal length fo can be expressed by Equation (17) below, using Equation (16) wherein fo is a focal length of the flat plane shaped (r=∞) reflection member 48 illustrated in FIG. 28 and using the relationship La=Lb.

$$1/La + 1/Lb = 1/f_0 \qquad \text{Equation (16)}$$

$$f_0 = La/2 \qquad \text{Equation (17)}$$

In the case of a lobster eye as a known optical element having a curvature r=R, a focal length $f_{Lob}$ is expressed by Equation (18) below.

$$f_{Lob} = R/2 \qquad \text{Equation (18)}$$

Accordingly, a focal length $f_R$ of the reflection member 48 with the curvature R is expressed by Equation (19) below, which can be rearranged so as to be expressed by Equation (20) below.

$$f_R = 1/f_0 + 1/f_{Lob} \qquad \text{Equation (19)}$$

$$f_R = 2\{La \cdot R/(La+R)\}La \qquad \text{Equation (20)}$$

In such cases, a distance Lb' to the formed image position can be expressed by Equation (22) below employing Equation (21) below.

$$1/La + 1/Lb = 1/f_R \qquad \text{Equation (21)}$$

$$Lb' = \{La \cdot R/(La+R)\}La \qquad \text{Equation (22)}$$

Accordingly, the magnification β is expressed by Equation (23) below.

$$\beta = R/(2La+R) \qquad \text{Equation (23)}$$

When the magnification β is expressed by Equation (23), the pupil size is β times, such that the calculated image angle of view is I/O times. Accordingly, the technology disclosed herein is effective even in the reflection member 48 imparted with the refractive power of 2/r.

The ophthalmic system 10 according to the present exemplary embodiment includes the display section 30 such as a display attached to an upper portion of the display device 40, and is configured to display the imaged image Im formed by the display section 30 toward the observer OP through the optical unit 42 and the reflection member 48 (see FIG. 1 and FIG. 3A to FIG. 3C). However, the image display system according to technology disclosed herein is not limited to a system in which the display section 30 is attached to an upper portion of the display device 40. For example, the display section 30 may be attached to a lower portion of the display device 40, and a configuration may be adopted to display the imaged image Im formed by the display section 30 toward the observer OP through the optical unit 42 and the reflection member 48 with an optical axis running from bottom to top in the display device 40. Namely, the position where the display section 30 is attached to the display device 40 may be any position on the display device 40, and the optical axis direction toward the display device 40 may be configured so as to face in any direction with respect to the display device 40.

Note that although in the present exemplary embodiment an ophthalmic system applied with an ophthalmic device has been described as an example of an image display system according to technology disclosed herein, the image display system according to technology disclosed herein is not limited to an ophthalmic system applied with an ophthalmic device. Namely, in the technology disclosed herein, an image display device according to technology disclosed herein is applicable to any device for displaying images, and an image display system according to technology disclosed herein is applicable to any system equipped with a device for displaying images.

Explanation next follows regarding examples of image display devices to which the technology disclosed herein is applicable, and to application examples of image display systems equipped with such image display devices.

A first application example is an example of application to a display device of an observation system for observing distant objects using an optical instrument such as binoculars, a periscope, or the like. In particular, an image display device or image display system according to the technology disclosed herein functions effectively when applied to binoculars.

Figure 29:
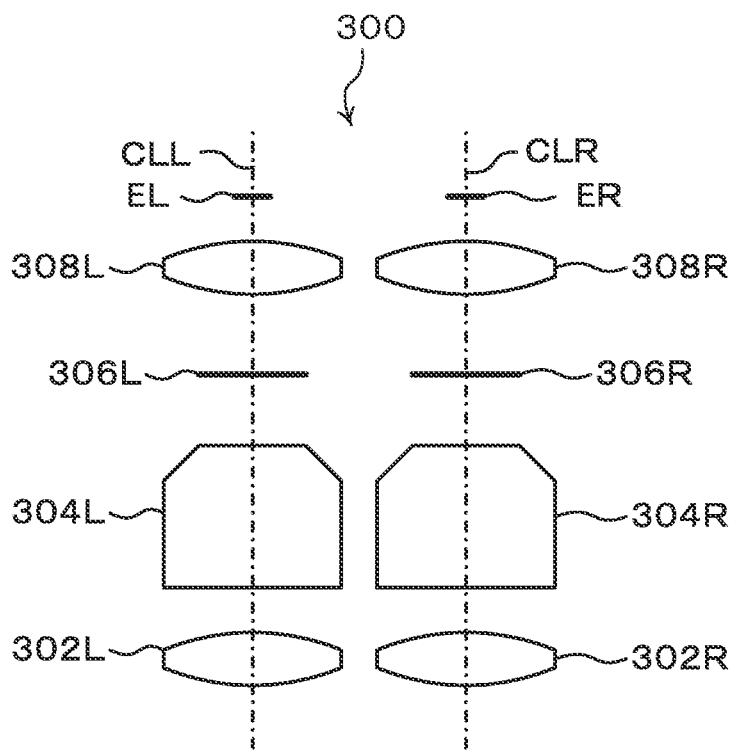
FIG. 29 is a schematic diagram illustrating a configuration of ordinary binoculars according to an exemplary embodiment.
Figure 30:
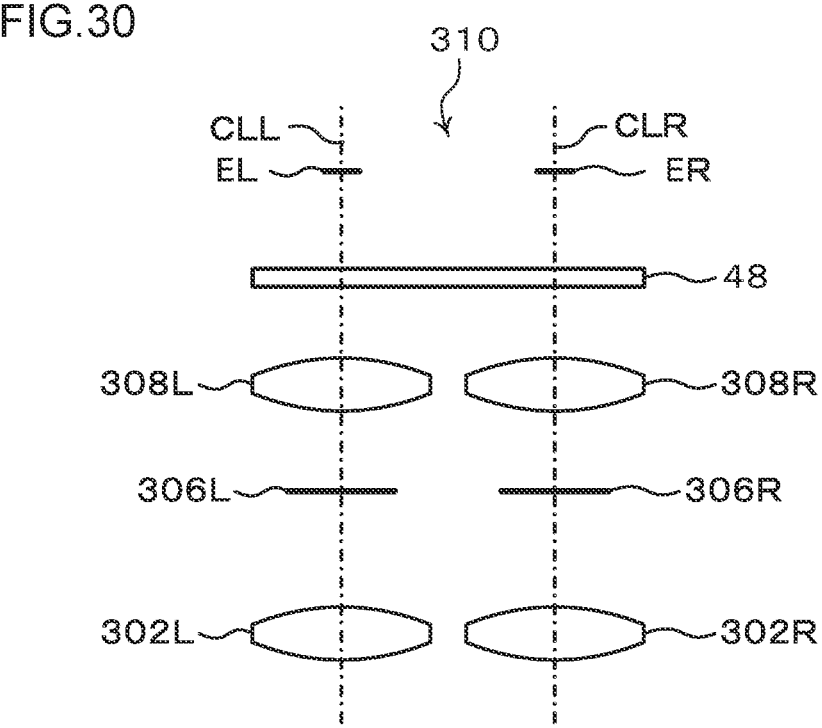
FIG. 30 is a schematic diagram illustrating a configuration of a first example binoculars applied with an image display device or image display system according to an exemplary embodiment.

FIG. 29 schematically illustrates configuration of ordinary binoculars 300. FIG. 30 schematically illustrates configuration of a first example binoculars 310 applied with an image display device or image display system according to the technology disclosed herein.

As illustrated in FIG. 29, the ordinary binoculars 300 include left-eye and right-eye objective lenses 302L, 302R and ocular lenses 308L, 308R to magnify and observe a distant object using both eyes. FIG. 29 illustrates left and right pupils EL, ER of the binoculars 300. In the binoculars 300, primary images 306L, 306R of an object magnified by the objective lenses 302L, 302R are further magnified by the ocular lenses 308L, 308R. However, since the images magnified by the objective lenses 302L, 302R and the ocular lenses 308L, 308R would be perceived as upside-down images, optical elements 304 such as Porro prisms or Dach prisms are employed to convert the upside-down images into right-way-up images.

In the binoculars 310 applied with an image display device or image display system according to the technology disclosed herein, since the images are inverted by the reflection member 48, the optical elements 304 such as Porro prisms or Dach prisms may be omitted.

Figure 31:
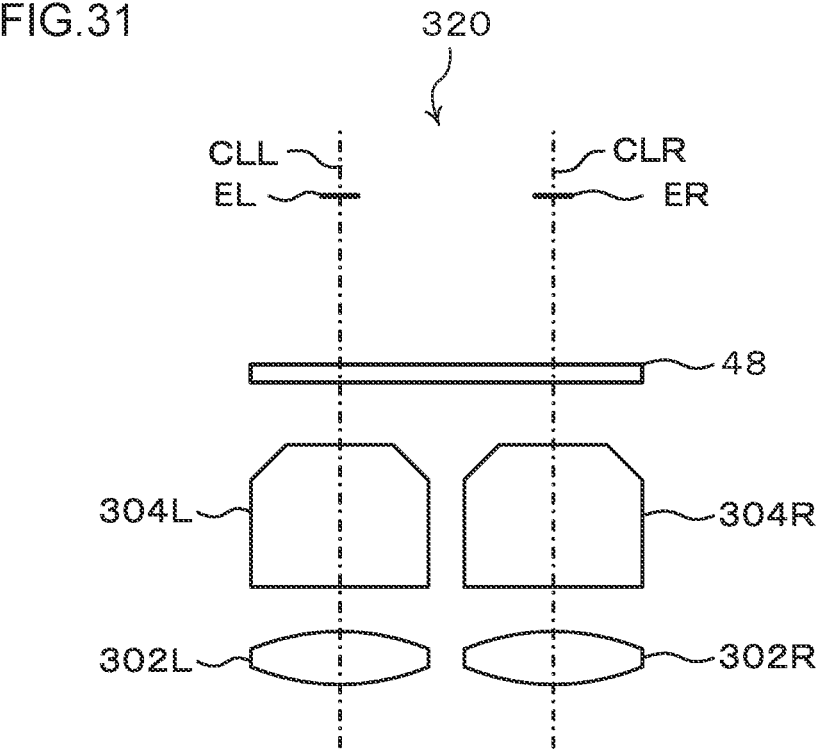
FIG. 31 is a schematic diagram illustrating a configuration of a second example binoculars applied with an image display device or image display system according to an exemplary embodiment.

FIG. 31 schematically illustrates configuration of a second example binoculars 320 applied with an image display device or image display system according to the technology disclosed herein. The second example binoculars 320 illustrated in FIG. 31 are configured by disposing the reflection member 48 instead of the ocular lenses 308L, 308R of the ordinary binoculars 300. Although in the binoculars 320 converging light is emit from the optical elements 304, this is converted into divergent light by the reflection member 48, enabling an image to be viewed by the observer OP performing eye adjustment.

Figure 32:
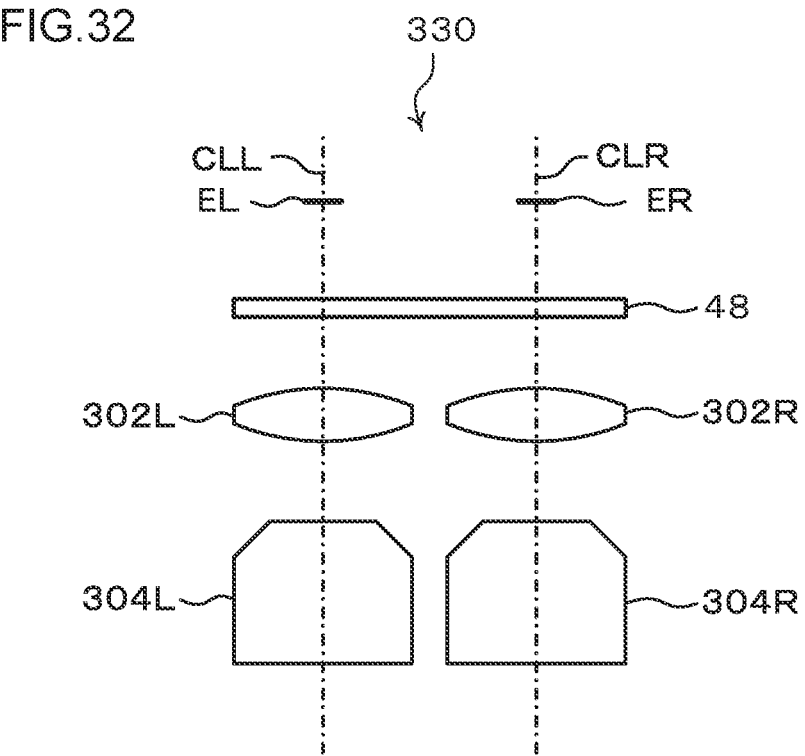
FIG. 32 is a schematic diagram illustrating a configuration of a third example binoculars applied with an image display device or image display system according to an exemplary embodiment.

FIG. 32 schematically illustrates configuration of a third example binoculars 330 applied with an image display device or image display system according to the technology disclosed herein. The third example binoculars 330 illustrated in FIG. 32 have a configuration in which the objective lenses 302L, 302R and the optical elements 304L, 304R of the second example binoculars 320 have been swapped over. Although the binoculars 330 also emit converging light from the objective lenses 302 (302L, 302R), this is converted into divergent light by the reflection member 48, enabling an image to be viewed by the observer OP performing eye adjustment.

By applying the image display device or the image display system according to the technology disclosed herein to binoculars for observing distant objects, the observer OP is able to observe distant objects in a non-contact state with the binoculars, suppressing the observer OP from feeling unsettled by contact that occurs. Moreover, the apparent size of an image being viewed with the binoculars does not change, and so the head of the observer OP is able to move within the eye points (eye boxes). There is accordingly a larger permitted range of operation of the binoculars.

A second application example is an example of application to an ordinary optical binocular microscope.

Figure 33:
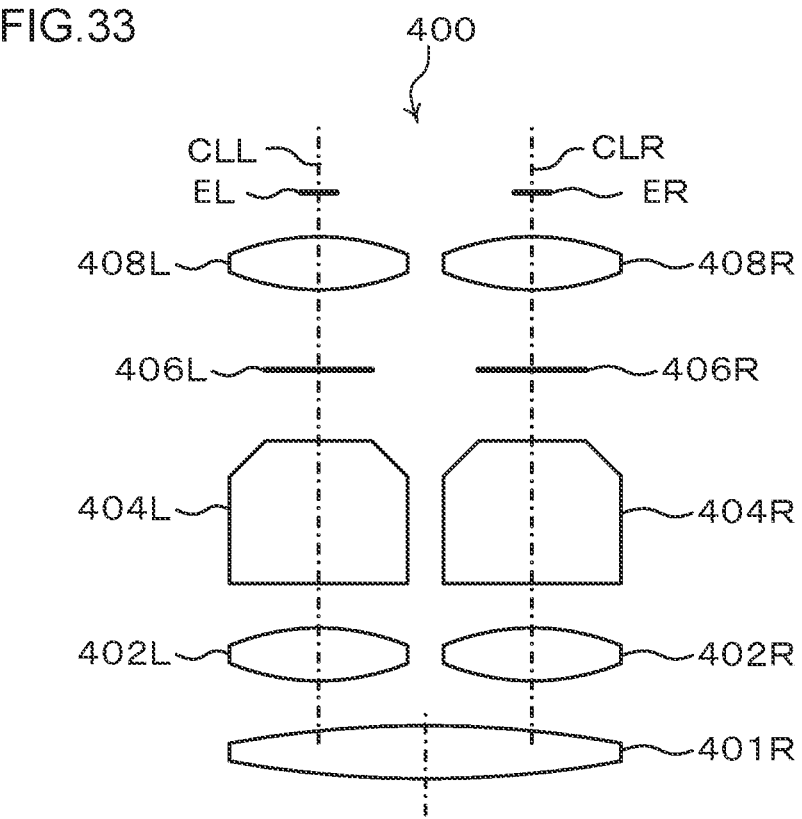
FIG. 33 schematically illustrates a configuration of an ordinary optical microscope according to an exemplary embodiment.
Figure 34:
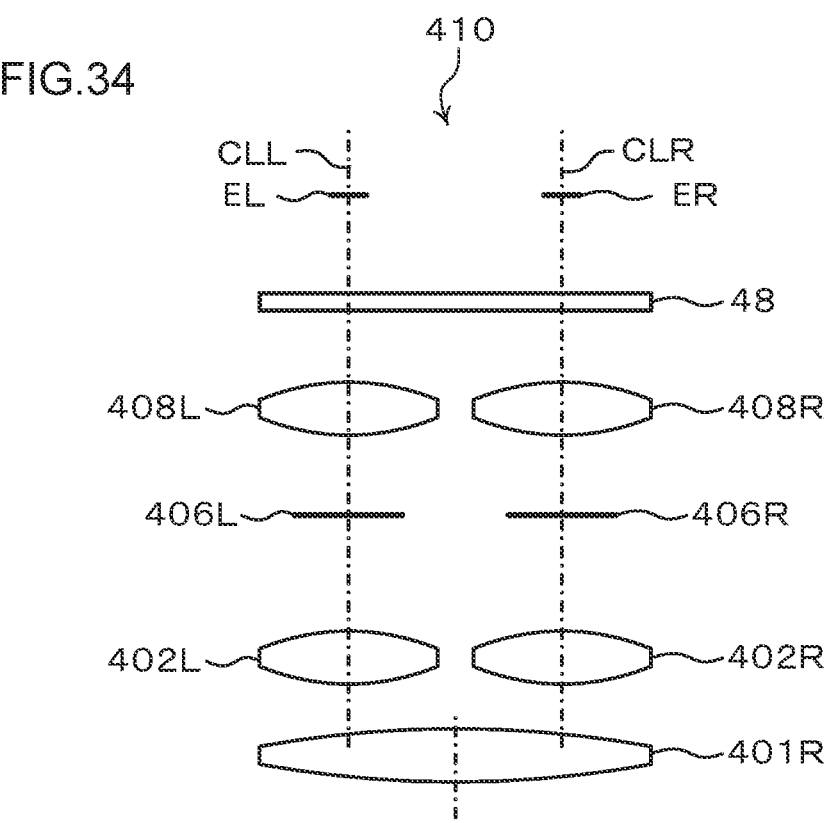
FIG. 34 is a schematic diagram illustrating a configuration of a first example optical microscope applied with an image display device or image display system according to an exemplary embodiment.

FIG. 33 schematically illustrates configuration of an ordinary optical microscope 400. FIG. 34 schematically illustrates configuration of a first example optical microscope 410 applied with an image display device or image display system according to the technology disclosed herein.

As illustrated in FIG. 33, the ordinary optical binocular microscope 400 includes a first objective lens 401R, left-eye and right-eye second objective lenses 402L, 402R, and left-eye and right-eye ocular lenses 408L, 408R to observe a magnified object with both eyes. FIG. 33 also illustrates left and right pupils EL, ER of the optical microscope 400. In the optical microscope 400, primary images 406L, 406R of an object magnified by the first objective lens 401R and the second objective lenses 402L, 402R are further magnified by the ocular lenses 408L, 408R. However, since the images magnified by the first objective lens 401R, the second objective lenses 402L, 402R and the ocular lenses 408L, 408R would be perceived as upside-down images, optical elements 404L, 404R such as Porro prisms or Dach prisms are employed to convert the upside-down images into right-way-up images.

However, in the optical microscope 410 applied with an image display device or image display system according to the technology disclosed herein, since the images are inverted by the reflection member 48, the optical elements 404L, 404R such as Porro prisms or Dach prisms may be omitted.

Figure 35:
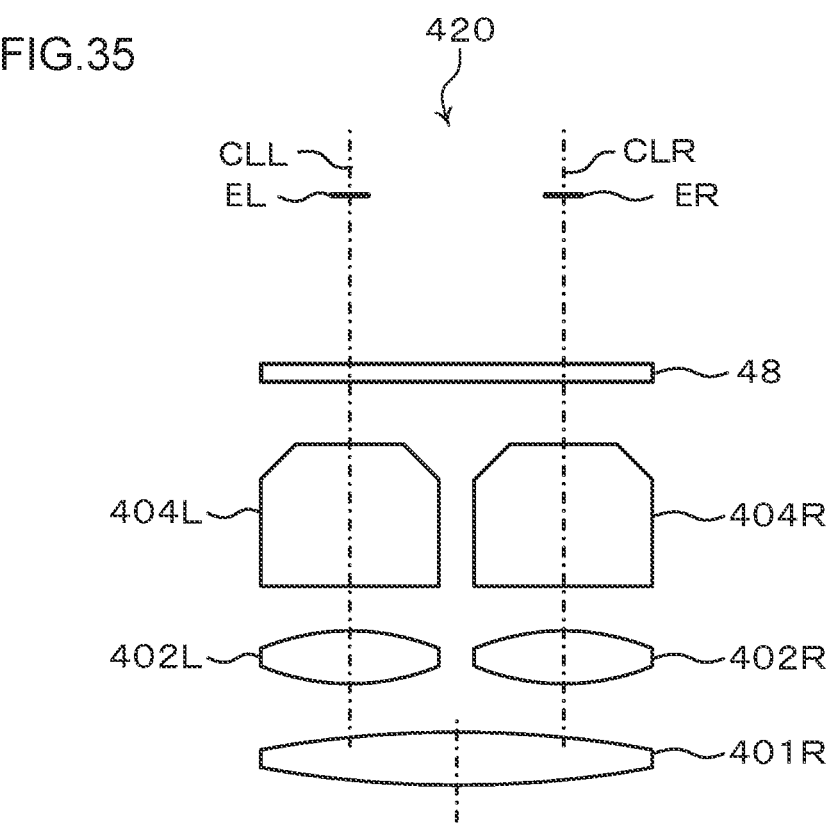
FIG. 35 is a schematic diagram illustrating a configuration of a second example optical microscope applied with an image display device or image display system according to an exemplary embodiment.

FIG. 35 schematically illustrates configuration of a second example optical microscope 420 applied with an image display device or image display system according to the technology disclosed herein. The third example optical microscope 420 illustrated in FIG. 35 is configured by disposing the reflection member 48 instead of the ocular lenses 408L, 408R of the ordinary optical microscope 400. Although the optical microscope 420 emits converging light from the optical elements 404L, 404R, this is converted into divergent light by the reflection member 48, enabling an image to be viewed by the observer OP performing eye adjustment.

Figure 36:
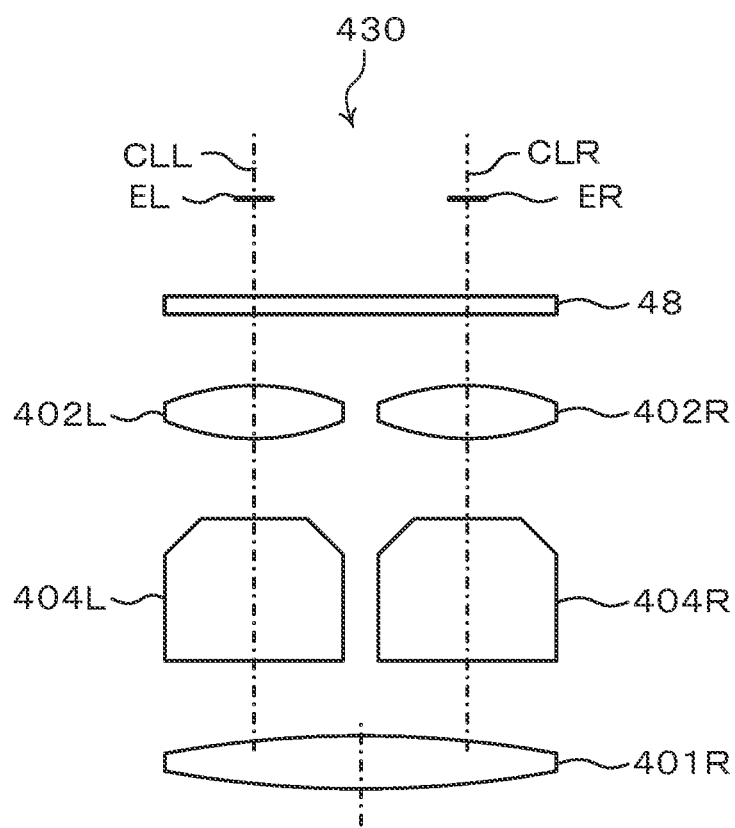
FIG. 36 is a schematic diagram illustrating a configuration of a third example optical microscope applied with an image display device or image display system according to an exemplary embodiment.

FIG. 36 schematically illustrates configuration of a third example optical microscope 430 applied with an image display device or image display system according to the technology disclosed herein. The third example optical microscope 430 illustrated in FIG. 36 has a configuration in which the second objective lenses 402L, 402R and the optical elements 404L, 404R of the optical microscope 420 of the second example have been swapped over. Although the optical microscope 430 also emits converging light from the second objective lenses 402L, 402R, this is converted into divergent light by the reflection member 48, enabling an image to be viewed by adjusting the eyes of the observer OP.

By applying the image display device or the image display system according to the technology disclosed herein to a binocular optical microscope in this manner, the observer OP is able to observe objects in a non-contact state with the binocular optical microscope, suppressing the observer OP from feeling unsettled by contact that occurs. Moreover, the apparent size of an image being viewed with the binocular optical microscope does not change, and so the head of the observer OP is able to move within the eye points (eye boxes). There is accordingly a larger permitted range of operation of the binocular optical microscope.

The display section described above may be understood to be an image presentation section.

Another aspect of the present exemplary embodiment is an image display device including a left-eye optical unit, a right-eye optical unit, an image presentation section, and a reflection section. In the left-eye optical unit a left-eye image region for displaying a left-eye image is disposed on an incident side of the left-eye optical unit and a left-eye exit pupil is formed outside an outermost lens on an exit side of the left-eye optical unit. In the right-eye optical unit a right-eye image region for displaying a right-eye image is disposed on an incident side of the right-eye optical unit and a right-eye exit pupil is formed outside an outermost lens on an exit side of the right-eye optical unit. The image presentation section causes a convergence angle to arise between two eyes when the left-eye image region is viewed through the left-eye optical unit and the right-eye image region is viewed through the right-eye optical unit by presenting the left-eye image region such that its region center is disposed in a focal plane of the left-eye optical unit at a position away from an optical axis of the left-eye optical unit, and by presenting the right-eye image region such that its region center is disposed in a focal plane of the right-eye optical unit at a position away from an optical axis of the right-eye optical unit. The reflection section reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

Another aspect of the present exemplary embodiment is an image display device including a left-eye optical unit, a right-eye optical unit, an image presentation section, and a reflection section. In the left-eye optical unit a left-eye image region for displaying a left-eye image is disposed on an incident side of the left-eye optical unit and a left-eye exit pupil is formed outside an outermost lens on an exit side of the left-eye optical unit. In the right-eye optical unit a right-eye image region for displaying a right-eye image is disposed on an incident side of the right-eye optical unit and a right-eye exit pupil is formed outside an outermost lens on an exit side of the right-eye optical unit. The image presentation section causes a convergence angle to arise between two eyes when the left-eye image region is viewed through the left-eye optical unit and the right-eye image region is viewed through the right-eye optical unit by presenting the left-eye image region such that its region center is disposed in a focal plane of the left-eye optical unit and on an optical axis of the left-eye optical unit, and by presenting the right-eye image region such that its region center is disposed in a focal plane of the right-eye optical unit and on an optical axis of the right-eye optical unit. The image presentation section causes the optical axis of the left-eye optical unit and the optical axis of the right-eye optical unit to intersect each other at the exit sides of the left-eye optical unit and the right-eye optical unit. The reflection section reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

Note that although exemplary embodiments related to the technology disclosed herein have been described, the scope of technology disclosed herein is not limited to the scope of the above exemplary embodiments. Various modifications and improvements can be made to the exemplary embodiments described above without departing from the scope of the gist of the technology disclosed herein, and these modifications and improvements are included within the scope of the technology disclosed herein. Moreover, all publications, patent applications and technical standards mentioned in the present specification are incorporated by reference in the present specification to the same extent as if each individual publication, patent application, or technical standard was specifically and individually indicated to be incorporated by reference.

The invention claimed is:

1. An image display device comprising:
    a left-eye optical unit having a left-eye image region for displaying a left-eye image disposed on an incident side of the left-eye optical unit and having a left-eye exit pupil disposed outside an outermost lens on an exit side of the left-eye optical unit;
    a right-eye optical unit having a right-eye image region for displaying a right-eye image disposed on an incident side of the right-eye optical unit and having a right-eye exit pupil disposed outside an outermost lens on an exit side of the right-eye optical unit;
    a display section that causes a convergence angle to arise between two eyes when the left-eye image region is viewed through the left-eye optical unit and the right-eye image region is viewed through the right-eye optical unit, by presenting the left-eye image region such that its region center is disposed in a focal plane of the left-eye optical unit at a position away from an optical axis of the left-eye optical unit, and by presenting the right-eye image region such that its region center is disposed in a focal plane of the right-eye optical unit at a position away from an optical axis of the right-eye optical unit; and
    a reflection section that reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

2. The image display device of claim 1, further comprising:
    a distance varying section that varies at least one distance of a distance between the region center of the left-eye image region and the region center of the right-eye image region or a distance between an optical axis of the left-eye optical unit and an optical axis of the right-eye optical unit;
    wherein the display section presents the left-eye image region and the right-eye image region in a state in which the at least one distance has been varied by the distance varying section.

3. The image display device of claim 2, wherein, in a case in which the convergence angle caused to arise between the two eyes is to be increased, the distance varying section changes the distance between the region center of the left-eye image region and the region center of the right-eye image region from a current first distance to a second distance greater than the first distance.

4. The image display device of claim 2, wherein the distance varying section varies the distance between the region center of the left-eye image region and the region center of the right-eye image region so as to increase the convergence angle as the distance between the region center of the left-eye image region and the region center of the right-eye image region increases.

5. An image display device comprising:
a left-eye optical unit having a left-eye image region for displaying a left-eye image-disposed on an incident side of the left-eye optical unit and having a left-eye exit pupil disposed outside an outermost lens on an exit side of the left-eye optical unit;
a right-eye optical unit having a right-eye image region for displaying a right-eye image-disposed on an incident side of the right-eye optical unit and having a right-eye exit pupil disposed outside an outermost lens on an exit side of the right-eye optical unit;
a display section that causes a convergence angle to arise between two eyes when the left-eye image region is viewed through the left-eye optical unit and the right-eye image region is viewed through the right-eye optical unit, by presenting the left-eye image region such that its region center is disposed in a focal plane of the left-eye optical unit and on an optical axis of the left-eye optical unit and by presenting the right-eye image region such that its region center is disposed in a focal plane of the right-eye optical unit and on an optical axis of the right-eye optical unit, and that causes the optical axis of the left-eye optical unit and the optical axis of the right-eye optical unit to intersect each other at the exit sides of the left-eye optical unit and the right-eye optical unit; and
a reflection section that reflects light emitted from the left-eye optical unit to form a left-eye pupil at a position having a conjugate relationship to the left-eye exit pupil, and reflects light emitted from the right-eye optical unit to form a right-eye pupil at a position having a conjugate relationship to the right-eye exit pupil.

6. The image display device of claim 5, further comprising:
an angle varying section capable of varying an angle formed between the optical axis of the right-eye optical unit and the optical axis of the left-eye optical unit;
wherein the display section presents the left-eye image region and the right-eye image region in a state in which the angle has been varied by the angle varying section.

7. The image display device of-claim 1, wherein the display section presents a single image in which the left-eye image region and the right-eye image region are contiguous to each other.

8. The image display device of claim 1, wherein the display section independently presents a right-eye image and a left-eye image respectively in the right-eye image region and in the left-eye image region.

9. The image display device of claim 1, wherein:
at least one pupil of the left-eye pupil or the right-eye pupil formed by the reflection section is formed so as to so as satisfy a condition expressed by $d_0 > (1 + \tan\theta/\tan\Psi)^2 \cdot (\varphi/2 \tan\theta)$ wherein θ is a half-angle of a field of view angle, Ψ is an angle formed between an optical axis and a reflection surface of the reflection section, φ is a pupil diameter, and $d_0$ is a distance from the pupil to the reflection surface of the reflection section.

10. An image display device comprising:
an optical unit including a focal point on a light incident side at a position where an image of an object is displayed on a display section, and forming an exit pupil;
an optical element configured to reflect light emitted from the optical unit or to allow light emitted from the optical unit to pass through, and to relay the exit pupil to a position having a conjugate relationship to the exit pupil; and
a convergence angle adjustment mechanism configured to cause a convergence angle to arise between two eyes of an observer observing at the position of the exit pupil relayed by the optical element, by moving at least the display section.

11. The image display device of claim 10, further comprising a control section configured to control driving of the convergence angle adjustment mechanism so as to change the convergence angle.

12. The image display device of claim 11, wherein the control section is configured to invert the image of the object with respect to an image observed by an eye of the observer and to display the inverted image on the display section.

13. The image display device of claim 10, wherein the optical element is a recursive pass-through element or an optical image forming element.

14. The image display device of claim 10, wherein the convergence angle adjustment mechanism adjusts the convergence angle by moving the display section in a direction intersecting an optical axis of the optical unit.

15. The image display device of claim 10, wherein the convergence angle adjustment mechanism adjusts the convergence angle by moving the display section and the optical unit so as to change an incident angle of an optical axis of the optical unit with respect to a pupil plane of the exit pupil relayed by the optical element.

16. An image display system comprising:
the image display device of claim 1; and
an image processing section configured to acquire right-eye image information and left-eye image information and to perform image processing such that a right-eye image region and a left-eye image region formed based on the acquired right-eye image information and the acquired left-eye image information are inverted.

17. The image display system of claim 16, wherein:
the right-eye image information and the left-eye image information are image information expressing an imaged image in which an anterior eye portion of an examined eye has been imaged using a microscope; and
the image processing section is configured to perform image processing so as to invert both the right-eye image region and the left-eye image region in an image direction inverted by the microscope.

18. The image display system of claim 17, wherein:
the right-eye image information and the left-eye image information are image information expressing an image of a posterior eye portion of the examined eye imaged by installing a front-end optical element on an examined eye side of the microscope; and the image processing section performs image processing so as to swap over the right-eye image region and the left-eye image region.

19. An image display method of the image display device of claim 1, the image display method comprising execution of processing including presenting an inverted state of a right-eye image region and a left-eye image region formed based on right-eye image information and left-eye image information.

20. A non-transitory storage medium storing an image processing program to cause a computer to function as the image processing section of the image display system of claim 16.

* * * * *